(12) United States Patent
Filipovic et al.

(10) Patent No.: US 11,877,842 B1
(45) Date of Patent: *Jan. 23, 2024

(54) PERSONAL CLOUD WITH A PLURALITY OF MODULAR CAPABILITIES

(71) Applicant: Micro Mobio Corporation, Palo Alto, CA (US)

(72) Inventors: Zlatko Aurelio Filipovic, San Jose, CA (US); Weiping Wang, Palo Alto, CA (US); Adam James Wang, Palo Alto, CA (US); Guan-Wu Wang, Palo Alto, CA (US); Yi-Hung Chen, Hsinchu (TW)

(73) Assignee: Micro Mobio Corporation, Palo Alto, CA (US)

(*) Notice: Subject to any disclaimer, the term of this patent is extended or adjusted under 35 U.S.C. 154(b) by 11 days.

This patent is subject to a terminal disclaimer.

(21) Appl. No.: 17/694,446

(22) Filed: Mar. 14, 2022

Related U.S. Application Data

(63) Continuation-in-part of application No. 17/002,625, filed on Aug. 25, 2020, now Pat. No. 11,272,861, (Continued)

(51) Int. Cl.
*H04W 4/80* (2018.01)
*A61B 5/11* (2006.01)
(Continued)

(52) U.S. Cl.
CPC .............. *A61B 5/1117* (2013.01); *A61B 3/14* (2013.01); *A61B 5/0022* (2013.01); *A61B 5/01* (2013.01);
(Continued)

(58) Field of Classification Search
CPC ......... A61B 5/117; A61B 5/0022; A61B 5/01; A61B 5/332; A61B 5/02438; A61B 5/1112; A61B 3/14; A61B 5/6831; A61B 5/6898; A61B 2560/0252; A61B 2560/0257; A61B 2562/0219; A61B 5/742; A61B 5/748; G06F 1/1628; G06F 1/163; G06F 1/1632; G06F 1/1633; G06F 1/1698; G06F 1/183; G06F 21/32; G06F 21/70; H04B 1/385; H04B 1/3888; H04M 1/0254; H04M 1/72409; H04M 1/72412; H04M 1/185;
(Continued)

(56) References Cited

U.S. PATENT DOCUMENTS

| | | |
|---|---|---|
| 6,442,018 B1 | 8/2002 | Dinkin |
| 7,020,890 B1 | 3/2006 | Suematsu |

(Continued)

*Primary Examiner* — Hai V Nguyen
(74) *Attorney, Agent, or Firm* — ROARK IP

(57) ABSTRACT

A communication device comprising: a first unit having a first antenna, a second antenna, and a first signal transmitting and receiving circuitry; a second unit having a third antenna, a fourth antenna, and a second signal transmitting and receiving circuitry, wherein the second unit is located in proximity to the first unit; and wherein the second unit is capable of receiving signals at a first signal frequency, down converting the signals to a second signal frequency, and relaying the signals through a barrier to the first unit. Wherein the first signal frequency is in the millimeter wave range and the second signal frequency is in the microwave range.

20 Claims, 27 Drawing Sheets

Related U.S. Application Data which is a continuation-in-part of application No. 16/198,679, filed on Nov. 21, 2018, now abandoned, which is a continuation-in-part of application No. 15/418,727, filed on Jan. 28, 2017, now Pat. No. 10,159,430, which is a continuation of application No. 14/961,862, filed on Dec. 7, 2015, now Pat. No. 9,554,751, which is a continuation-in-part of application No. 14/036,729, filed on Sep. 25, 2013, now Pat. No. 9,207,715, which is a continuation-in-part of application No. 13/831,663, filed on Mar. 15, 2013, now Pat. No. 9,086,847.

(60) Provisional application No. 62/590,512, filed on Nov. 24, 2017, provisional application No. 61/705,383, filed on Sep. 25, 2012.

(51) Int. Cl.
| | |
|---|---|
| *G06F 1/16* | (2006.01) |
| *A61B 5/332* | (2021.01) |
| *H04B 1/3888* | (2015.01) |
| *H04M 1/02* | (2006.01) |
| *G06F 1/18* | (2006.01) |
| *G06F 21/32* | (2013.01) |
| *G06F 21/70* | (2013.01) |
| *A61B 3/14* | (2006.01) |
| *A61B 5/01* | (2006.01) |
| *A61B 5/00* | (2006.01) |
| *H04W 4/90* | (2018.01) |
| *A61B 5/024* | (2006.01) |
| *H04B 1/3827* | (2015.01) |
| *H02J 50/10* | (2016.01) |
| *H04M 1/18* | (2006.01) |
| *H04M 1/72409* | (2021.01) |
| *H04M 1/72412* | (2021.01) |
| *H04W 84/04* | (2009.01) |
| *H04W 84/12* | (2009.01) |
| *H04W 88/08* | (2009.01) |

(52) U.S. Cl.
CPC ........ *A61B 5/02438* (2013.01); *A61B 5/1112* (2013.01); *A61B 5/332* (2021.01); *A61B 5/6831* (2013.01); *A61B 5/6898* (2013.01); *A61B 5/742* (2013.01); *A61B 5/748* (2013.01); *G06F 1/163* (2013.01); *G06F 1/1628* (2013.01); *G06F 1/1632* (2013.01); *G06F 1/1633* (2013.01); *G06F 1/1698* (2013.01); *G06F 1/183* (2013.01); *G06F 21/32* (2013.01); *G06F 21/70* (2013.01); *H02J 50/10* (2016.02); *H04B 1/385* (2013.01); *H04B 1/3888* (2013.01); *H04M 1/0254* (2013.01); *H04W 4/90* (2018.02); *A61B 2560/0242* (2013.01); *A61B 2560/0252* (2013.01); *A61B 2560/0257* (2013.01); *A61B 2562/0219* (2013.01); *H04M 1/185* (2013.01); *H04M 1/72409* (2021.01); *H04M 1/72412* (2021.01); *H04W 4/80* (2018.02); *H04W 84/04* (2013.01); *H04W 84/12* (2013.01); *H04W 88/08* (2013.01)

(58) Field of Classification Search
CPC ....... H04W 4/80; H04W 84/04; H04W 84/12; H04W 88/08
See application file for complete search history.

(56) References Cited

U.S. PATENT DOCUMENTS

| | | | |
|---|---|---|---|
| 7,265,970 B2 | 9/2007 | Jordan | |
| 7,558,057 B1 | 7/2009 | Naksen et al. | |
| 7,743,999 B1 | 6/2010 | Griffin | |
| 7,791,312 B2 | 9/2010 | Kook | |
| 7,936,147 B2 | 5/2011 | Kook | |
| 8,035,577 B2 | 10/2011 | Lafarre et al. | |
| 8,328,055 B1 | 12/2012 | Snyder | |
| 8,605,421 B2 | 12/2013 | Verschoor et al. | |
| 8,896,992 B2 | 11/2014 | Sherlock | |
| 8,929,085 B2 | 1/2015 | Franklin et al. | |
| 9,086,847 B2 * | 7/2015 | Filipovic | G06F 1/163 |
| 9,207,715 B2 * | 12/2015 | Filipovic | G06F 1/1628 |
| 9,331,875 B2 | 5/2016 | Ashrafi | |
| 9,374,788 B2 | 6/2016 | Singamsetti | |
| RE46,111 E | 8/2016 | Koon | |
| 9,525,524 B2 | 12/2016 | Barzegar | |
| 9,537,345 B2 | 1/2017 | Wang | |
| 9,554,751 B2 * | 1/2017 | Filipovic | H04M 1/724094 |
| 9,622,133 B1 | 4/2017 | Guvenc | |
| 9,624,706 B2 | 4/2017 | Jacobs | |
| 9,641,208 B2 | 5/2017 | Sela | |
| 9,671,835 B2 * | 6/2017 | Filipovic | A61B 5/02438 |
| 9,773,601 B2 | 9/2017 | Breiwa | |
| 9,918,673 B2 | 3/2018 | Dugan | |
| 9,986,440 B2 | 5/2018 | Guvenc | |
| 9,999,038 B2 | 6/2018 | Barzegar | |
| 10,014,948 B2 | 7/2018 | Ashrafi | |
| 10,020,891 B2 | 7/2018 | Ashrafi | |
| 10,153,845 B2 | 12/2018 | Ashrafi | |
| 10,159,430 B1 * | 12/2018 | Filipovic | H04W 4/90 |
| 10,187,156 B2 | 1/2019 | Ashrafi | |
| 10,192,665 B2 | 1/2019 | Breiwa | |
| 10,244,098 B2 | 3/2019 | Muthukumar | |
| 10,271,260 B2 * | 4/2019 | Koshy | G01S 1/045 |
| 10,313,164 B2 | 6/2019 | Mody | |
| 10,326,488 B2 | 6/2019 | Wojcik | |
| 10,374,710 B2 | 8/2019 | Ashrafi | |
| 10,425,159 B2 | 9/2019 | Leiba | |
| 10,437,295 B1 * | 10/2019 | Filipovic | H04M 1/724092 |
| 10,448,276 B2 | 10/2019 | Chun | |
| 10,547,386 B2 | 1/2020 | Ashrafi | |
| 10,631,343 B2 * | 4/2020 | Wu | H04W 64/003 |
| 10,643,962 B1 * | 5/2020 | Ichitsubo | H03F 3/72 |
| 10,778,332 B2 | 9/2020 | Ashrafi | |
| 10,784,952 B2 | 9/2020 | Huang | |
| 10,784,962 B2 | 9/2020 | Ashrafi | |
| 10,840,964 B2 * | 11/2020 | Mizunuma | H04B 7/04 |
| 10,840,997 B2 | 11/2020 | Cheng | |
| 10,683,458 B2 | 12/2020 | Black | |
| 10,903,906 B2 | 1/2021 | Ashrafi | |
| 10,938,360 B1 * | 3/2021 | Wang | H04B 1/006 |
| 11,036,262 B1 * | 6/2021 | Ichitsubo | H03G 3/3042 |
| 11,058,326 B1 * | 7/2021 | Filipobic | A61B 5/6831 |
| 11,172,516 B2 * | 11/2021 | Wu | H04J 13/0062 |
| 11,179,063 B1 * | 11/2021 | Filipovic | G06F 1/1628 |
| 11,272,861 B1 * | 3/2022 | Filipovic | A61B 5/1117 |
| 11,350,307 B2 * | 5/2022 | Boyapalle | H04W 72/56 |
| 11,404,788 B1 * | 8/2022 | Wang | H01Q 9/0414 |
| 11,445,054 B2 * | 9/2022 | Kosa | A63F 13/98 |
| 11,456,770 B2 * | 9/2022 | Koga | H01Q 9/0414 |
| 11,492,114 B1 * | 11/2022 | Filipovic | G08G 5/0013 |
| 11,515,617 B1 * | 11/2022 | Ichitsubo | H01Q 9/0407 |
| 11,528,046 B2 * | 12/2022 | Caporal Del Barrio | H04B 1/3838 |
| 11,553,857 B1 * | 1/2023 | Filipovic | G06F 1/1633 |
| 11,642,045 B1 * | 5/2023 | Filipovic | H02J 50/20 455/702 |
| 2003/0115475 A1 | 6/2003 | Russo et al. | |
| 2004/0184466 A1 | 9/2004 | Chang et al. | |
| 2005/0221764 A1 | 10/2005 | Shen | |
| 2006/0050475 A1 | 2/2006 | Chen | |
| 2008/0131893 A1 | 8/2008 | Maraganore | |
| 2009/0261778 A1 | 10/2009 | Kook | |
| 2010/0289450 A1 | 11/2010 | Kook | |
| 2012/0088557 A1 | 4/2012 | Liang | |

(56) References Cited

U.S. PATENT DOCUMENTS

| | | | | |
|---|---|---|---|---|
| 2012/0212896 | A1 | 8/2012 | Schulz | |
| 2012/0218695 | A1 | 8/2012 | Sakai | |
| 2012/0235635 | A1 | 9/2012 | Sato | |
| 2012/0241247 | A1 | 9/2012 | Choe | |
| 2012/0247989 | A1 | 10/2012 | Cooper | |
| 2012/0249064 | A1 | 10/2012 | Negishi et al. | |
| 2012/0252411 | A1 | 10/2012 | Johnsgard et al. | |
| 2012/0262345 | A1 | 10/2012 | Byun et al. | |
| 2012/0268891 | A1 | 10/2012 | Cencioni | |
| 2012/0270600 | A1 | 10/2012 | Zelson | |
| 2012/0281356 | A1 | 11/2012 | Brewer et al. | |
| 2012/0299966 | A1 | 11/2012 | Kim et al. | |
| 2013/0063873 | A1 | 3/2013 | Wodrich et al. | |
| 2013/0076614 | A1 | 3/2013 | Ive et al. | |
| 2013/0093388 | A1 | 4/2013 | Partovi | |
| 2013/0288600 | A1 | 10/2013 | Kuusilinna et al. | |
| 2014/0085815 | A1* | 3/2014 | Filipovic | G06F 1/163 361/679.56 |
| 2014/0086586 | A1 | 3/2014 | Voutilainen et al. | |
| 2014/0087788 | A1* | 3/2014 | Filipovic | A61B 5/1117 455/557 |
| 2014/0159867 | A1 | 6/2014 | Sartee et al. | |
| 2014/0285159 | A1 | 9/2014 | Wang | |
| 2014/0334098 | A1 | 11/2014 | Lauder et al. | |
| 2015/0130290 | A1 | 5/2015 | Park | |
| 2015/0141093 | A1 | 5/2015 | Sela | |
| 2015/0181413 | A1 | 6/2015 | Singamsetti | |
| 2015/0259078 | A1* | 9/2015 | Filipovic | G05D 1/0011 244/114 R |
| 2015/0289147 | A1 | 10/2015 | Lou | |
| 2016/0106370 | A1* | 4/2016 | Filipovic | A61B 5/1112 340/870.07 |
| 2016/0294427 | A1 | 10/2016 | Wojcik | |
| 2017/0068290 | A1* | 3/2017 | Filipovic | G06F 1/183 |
| 2017/0118688 | A1 | 4/2017 | Guvenc | |
| 2017/0171761 | A1 | 6/2017 | Guvenc | |
| 2017/0195054 | A1 | 7/2017 | Ashrafi | |
| 2017/0238301 | A1 | 8/2017 | Nakazawa | |
| 2017/0366270 | A1 | 12/2017 | Ashrafi | |
| 2018/0026722 | A1 | 1/2018 | Ashrafi | |
| 2018/0123692 | A1 | 5/2018 | Leiba | |
| 2018/0124330 | A1 | 5/2018 | Muthukumar | |
| 2018/0139797 | A1 | 5/2018 | Chun | |
| 2018/0262272 | A1 | 9/2018 | Ashrafi | |
| 2019/0082495 | A1 | 3/2019 | Kim | |
| 2019/0098553 | A1* | 3/2019 | Koshy | H04B 7/0608 |
| 2019/0124698 | A1* | 4/2019 | Wu | H04W 8/005 |
| 2019/0173582 | A1 | 6/2019 | Ashrafi | |
| 2019/0173583 | A1 | 6/2019 | Ashrafi | |
| 2019/0221353 | A1 | 7/2019 | Hwang | |
| 2019/0372671 | A1 | 12/2019 | Ashrafi | |
| 2020/0083960 | A1 | 3/2020 | Ashrafi | |
| 2020/0145093 | A1 | 5/2020 | Cheng | |
| 2020/0145094 | A1 | 5/2020 | Huang | |
| 2020/0229245 | A1* | 7/2020 | Wu | H04W 64/003 |
| 2020/0244362 | A1 | 7/2020 | Ashrafi | |
| 2021/0044354 | A1 | 2/2021 | Ashrafi | |
| 2021/0250778 | A1 | 8/2021 | Tsutsui | |
| 2022/0107383 | A1* | 4/2022 | Rappaport | G01S 5/18 |
| 2022/0337278 | A1* | 10/2022 | Caporal Del Barrio | H04W 52/44 |

* cited by examiner

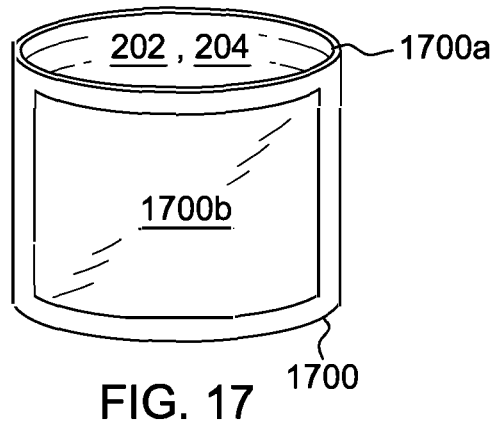
FIG. 17
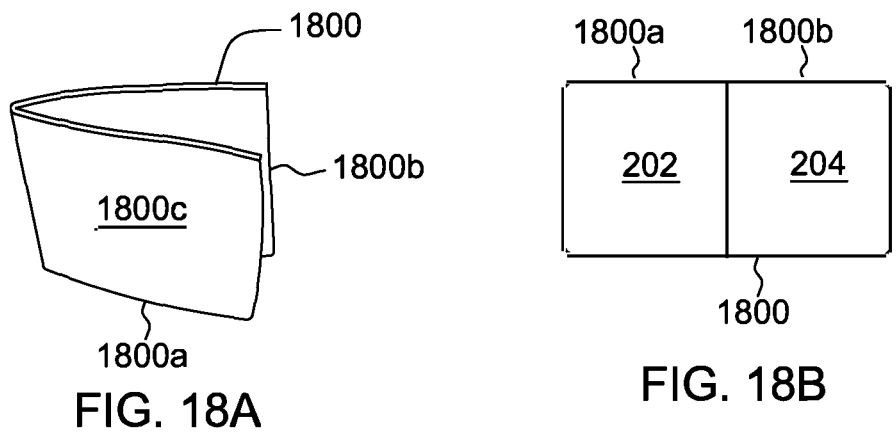
FIG. 18A
FIG. 18B
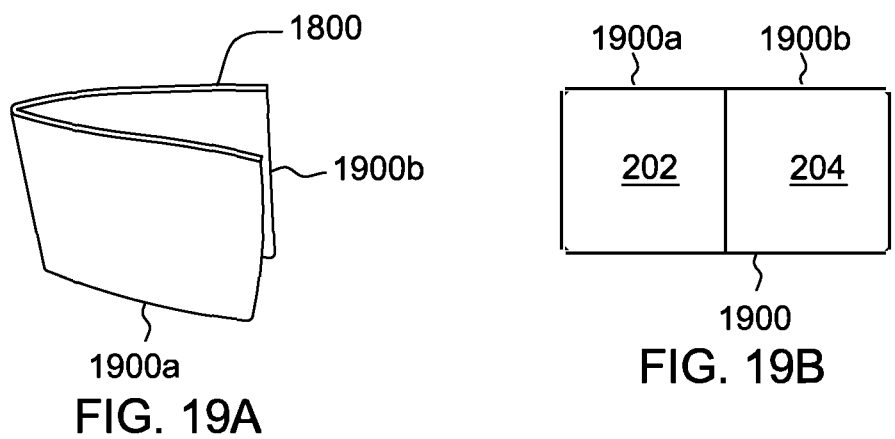
FIG. 19A
FIG. 19B

PERSONAL CLOUD WITH A PLURALITY OF MODULAR CAPABILITIES

PRIORITY CLAIM

This application is a Continuation-In-Part of U.S. patent application Ser. No. 17/002,625, filed on Aug. 25, 2020; which is a Continuation-In-Part of U.S. patent application Ser. No. 16/198,679, filed on Nov. 21, 2018; which is a non-provisional application of U.S. Provisional Patent Application No. 62/590,512, filed Nov. 24, 2017; and a Continuation-In-Part of U.S. patent application Ser. No. 15/418,727, filed on Jan. 28, 2017; which is a continuation of U.S. patent application Ser. No. 14/961,862, filed on Dec. 7, 2015, now U.S. Pat. No. 9,554,751; which is a continuation-in-part of U.S. patent application Ser. No. 14/036,729, filed Sep. 25, 2013, now U.S. Pat. No. 9,207,715; which claims the priority of U.S. patent application Ser. No. 13/831,663, filed Mar. 15, 2013, now U.S. Pat. No. 9,086,847; which claims priority to U.S. Provisional Patent Application Ser. No. 61/705,383, filed Sep. 25, 2012; the aforementioned applications being incorporated herein by reference in their entirety.

FIELD OF THE DISCLOSURE

The present disclosure relates generally to a system and method of mobile computing and, in particular, in one or more embodiments, the present disclosure relates to structures having a plurality of modular capabilities.

BACKGROUND

There are presently a wide variety of portable electronic devices 102 as disclosed in FIG. 1A. The portable electronic devices may include cellphones such as the iPhone®, Nexus, Lumia and the like and tablet personal computers (PCs) such as the iPad®, Kindle® and similar type devices. These portable electronic devices are often protected by a simple case cover 104 as disclosed in FIG. 1B. These prior art case covers 104 typically do not contain any functional components beyond the protective cover itself.

SUMMARY

Aspects of the disclosure include a communication device comprising: a first unit having a first antenna, a second antenna, and a first signal transmitting and receiving circuitry; a second unit having a third antenna, a fourth antenna, and a second signal transmitting and receiving circuitry, wherein the second unit is located in proximity to the first unit; wherein the first unit is capable of receiving signals at a first signal frequency at the first antenna in the frequency range of about 17 GigaHertz (GHz) to 300 GHz, passing the signal through an automatic gain controller to control the gain of the signals, down converting the signals to a second signal frequency in the frequency range of about 1 GHz to 9 GHz, and relaying the signals from the second antenna through a barrier to the second unit; and wherein the second unit is capable of receiving the signals at the third antenna, passing the signals in the frequency range of 1 GHz to 9 GHz to the fourth antenna for transmission.

BRIEF DESCRIPTION OF THE DRAWINGS

FIG. 15 shows detachably mounted on a structure a mobile wireless computing device which functions like (and may actually be) an iPad®, iPhone®, PCtablet, Android® based tablet, TouchPad, Nexus 7®, Slate® or the like.

FIG. 17 illustrates an embodiment of the PCCC which has a screen mounted on a band such as a bracelet or sweatband.

FIGS. 18A and 18B illustrate an embodiment of the PCCC which have a screen mounted on a wallet.

FIGS. 19A and 19B illustrate an embodiment of the PCCC which have a wallet shape.

FIG. 30 illustrates such a problem of wireless signals trying to enter building 3000 to access wireless device 3002 which could be a mobile phone, Internet of Things (IoTs) device, and the like.

DETAILED DESCRIPTION

Although particular aspects or features of the following disclosure may be described with reference to one or more particular embodiments and/or drawings, it should be understood that such features are not limited to usage in the one or more particular embodiments or drawings with reference to which they are described, unless expressly specified otherwise. The functionality and/or the features of the embodiments that are described may be alternatively embodied by one or more other devices which are described but are not explicitly described as having such functionality/features.

Current mobile computing device covers are limited in their functionality by mainly providing protection from environmental shocks for mobile computing devices. However, the personal cloud cover case (or "PCCC") as disclosed in this application by providing electronic component accessories and functionalities to the cover case enhances the ability of a mobile computing device located inside the PCCC to provide cloud computing services. (Note: the acronym PCCC may be used herein with regard to the descriptions of FIGS. 14 through 23 to cover similar devices to the personal cloud cover case but not just in the shape of a case cover but rather a wallet, band, collar, key chain, tie, etc.). Cloud computing is the use of computing resources that are delivered as a service over a network (such as the Internet) and which reside in the "cloud". The mobile computing device in the case could be an iPad®, iPhone®, PC tablet, Android® based tablet, TouchPad, Nexus 7®, Slate® or the like.

Figure 1B:
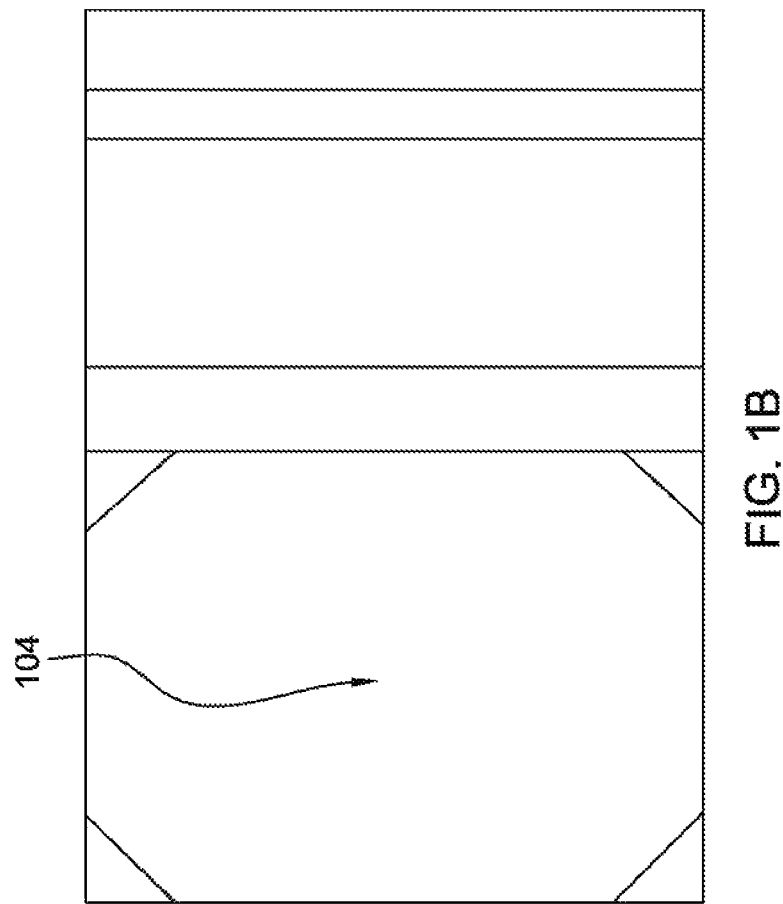
FIG. 1B is a front view of a prior art simple case cover for a mobile computing device.
Figure 1A:
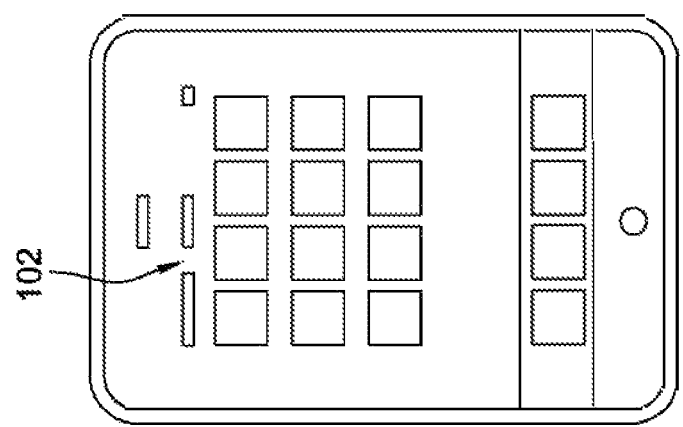
FIG. 1A is a front view of a prior art mobile computing device.
Figure 2A:
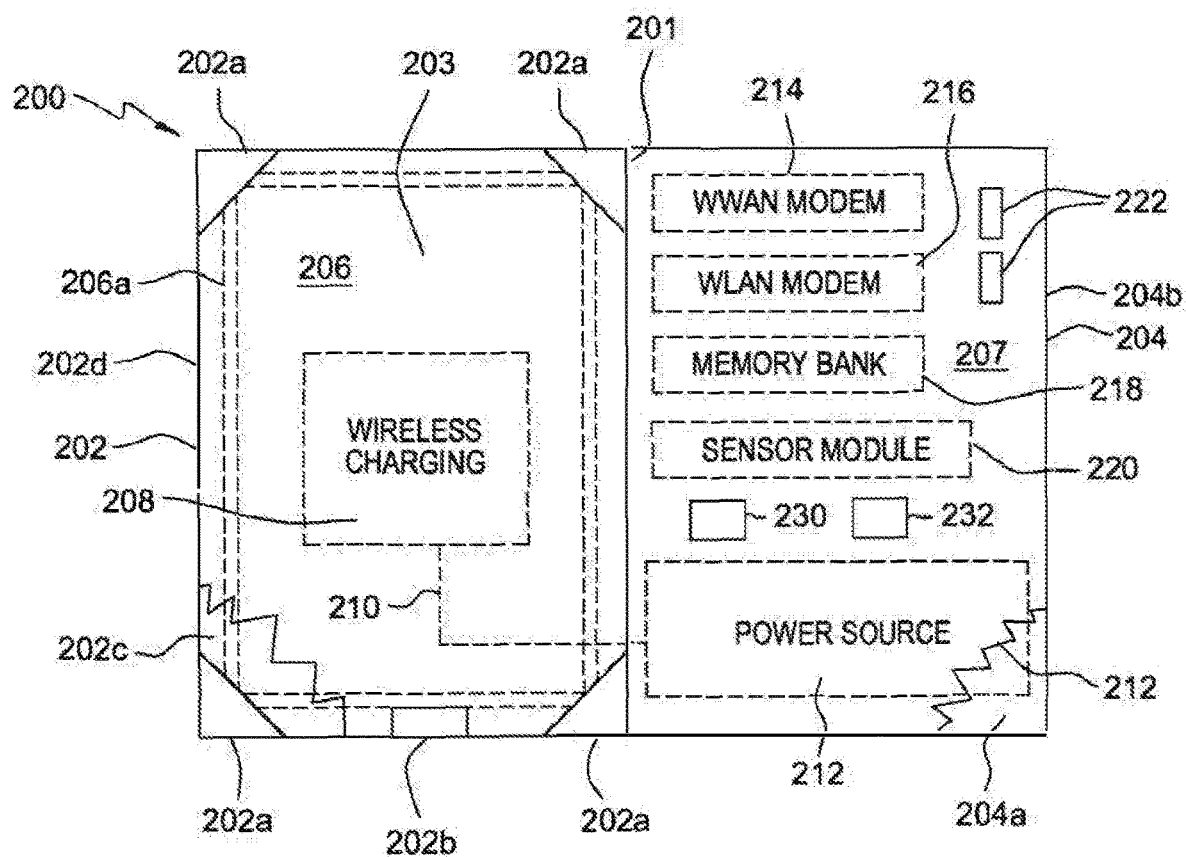
FIG. 2A is a front view of a personal cloud case cover (PCCC).

FIG. 2A is a front view of a PCCC 200 which is shown in an open position. The case 200 provides a personal cloud to the user and access to a wireless network (such as 3G, 4G, WiFi, SuperWifi, and similar technologies) of a mobile computing device (not shown) stored in the case 200. The case 200 may be made of any material (hard and/or soft) that makes the case lightweight but durable and resilient such as plastic, silicone, ceramic, fabric, leather, steel, aluminum, fiberglass, titanium, Kevlar, or rubber. The case 200 could be a continuous piece of material with a flexible (or bendable) area 201 located between two opposing panels (first panel 202 and second panel 204) which pivot together around a compartment 203 for containing the mobile computing device. In an alternative embodiment, the case 200 could be made up of plurality of attached sections (201, 202 and 204). First panel 202 also has 4 sleeves 202a to hold the mobile computing device in place in the case 200. In alternative embodiments, the mobile computing device could be attached to the PCCC 200 using a plurality of magnets (instead of the sleeves 202a) positioned under the mobile device, rubber straps or other similar attachment methods.

The first panel 202 is constructed in layers and includes inner first panel layer 202c, outer first panel layer 202d and embedded circuit board 206. Typically, from the front view the circuit board 206 cannot be seen since it is located underneath the first panel layer 202c shown in cutaway but which is designed to cover substantially the entire first panel 202. An antenna 206a is located on the circuit board 206 and may be in contact with the mobile communication device wirelessly, through physical contact or by connector 202b. Connector 202b is optional and in alternative embodiments it would not be present. The antenna 206a will allow for better transmission and reception on the part of the mobile communication device. The antenna 206a can be a "chip" antenna, printed circuit board (PCB) antenna or the like covering a plurality of wireless bands (e.g., 400 MHz-3.6 GHz). Alternatively, a PCB antenna may be used, and the antenna 206a will be printed directly onto the circuit board 206. Also located on the board 206 is a two-way wireless charging unit 208 which is in substantial proximity to the resting place of the mobile communication device in the cover 200. The charging unit 208 may be designed such that when the mobile communication device is in proximity to the charging unit an electromagnetic field generated by the charging unit pulls the communication device into proper position and alignment for optimal charging (i.e., charging coil alignment). The wireless charging unit 208 is connected through a bidirectional electrical link 210 to power source 212 located on a circuit board 207 embedded in the second panel 204. The bidirectional electrical link 210 is an example of the plurality of electrical connections that are made throughout the case 200 but which are not necessarily shown in the Figures. Link 210 might be in the form of a ribbon cable so as not to be damaged with the opening and closing of the case 200. The wireless charging unit 208 is capable of wirelessly charging the mobile communication device with power received from the power source 212 or wirelessly receive power from the mobile communication device and transfer it to the power source 212. The wireless charging unit 208 may operate by magnetic resonance, inductive charging, or power over radio frequency (RF) or similar wireless charging methods. The power source 212 is used to power the plurality of components located throughout the cover 200 and, as described, can also be used as a backup battery for the mobile computing device when the voltage in the battery of the mobile computing device falls below a predetermined level.

The second panel 204 can be made up of an inner second panel 204a and an outer second panel 204b containing the embedded circuit board 207 but which typically cannot be seen from a front view since it is covered by inner second panel layer 204a. The inner second panel layer 204a covers substantially the entire second panel 204 but is only partially shown in cutaway so as to illustrate the components mounted on the circuit board 207 in the outer second panel 204b. It should be understood that the inner second panel layer 204a and the outer second panel layer 204b can be coupled together by a variety of methods such as ultrasonic bonding, mechanical fasteners, adhesives, or solvents. In alternative embodiments, the inner second panel 204a may be entirely or substantially detachable from the outer second panel 204b; the inner second panel 204a may be a closure flap that is fastened close by means of adhesive, a snap button, or Velcro or the inner second panel 204a may not be present at all so as to allow easy access to the components mounted on the board 207 in the outer second panel 204b.

The case 200 may further be made up of a plurality of modules 214, 216, 218 and 220 mounted on the circuit board 207 which allow the PCCC 200 to have multi-functional capability. The modules may be made of low profile components which help minimize the thickness of the cover. The plurality of modules may be permanently mounted, may snap-into the board 207 or may be some combination thereof. First module 214 may include a wireless wide area network modem (WWAN). The WWAN could include baseband, a radio frequency integrated circuit (RFIC), a radio frequency front-end module (RF FEM), Envelope Tracking (ET), Power Management IC (PMIC), and other connected components to link the mobile computing device to a mobile network such as a 3G, 4G or future generation network. Second module 216 may include a wireless local area network (WLAN) modem for a mobile computing device to connect to a local router and then to 2G, 3G and 4G networks. The WLAN modem can be baseband, RFIC, RF FEM and other connectivity components. The case 200 may contain near field communications (NFC) technology which may be used for contactless short range communications based on RF identification standards (RFID) using magnetic field induction to enable communication between the electronic components in the case 200 over short distances such as a few centimeters. In other embodiments, the WLAN modem connection could be made using wireless protocols such as WiFi, SuperWiFi (i.e., the next generation WiFi with superior range), Bluetooth, wireless for high definition multimedia interface (WHDMI), or the like. Third module 218 may be internal storage such as solid-state drives (SSD) or flash memory (e.g., MultiMedia Card (MMC), electronic MMC (eMMC) or the like). Fourth module 220 may contain a sensor chip that is able to detect biometrics inputs such as finger prints, eye movement, face shape, and the like. Module 220 can be used for functions such as a security feature for allowing or denying access to the electronic components in the case, gaming, and medical purposes (e.g., measuring blood cell count and the like). The second panel 204 may also include a smart feature such as a synchronization input 230 (e.g., such as a button, touch screen, or the like) that allows the plurality of electronic components (e.g., module 218) in the PCCC 200 to be synched to other networked devices in the cloud when operated. This input 230 would primarily be used when a mobile communication device is not present in the PCCC 200. The input 230 may be used to backup data stored in the components of the PCCC 200. Reference 232 in FIG. 2A shows a controller which may be used with the mobile communication device or in the absence of the mobile device to control the electronic components in the PCCC 200. For example, in the synching process when input 230 is operated the controller 232 would direct the synching operation.

Figure 2B:
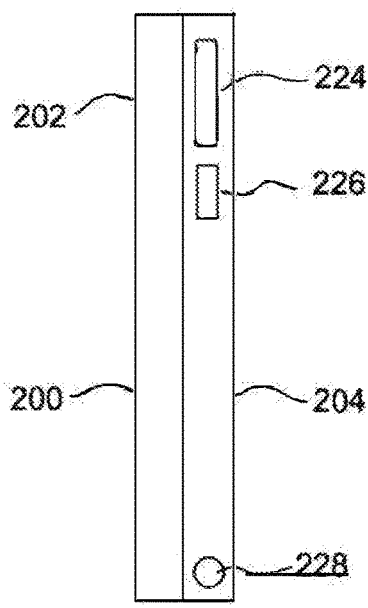
FIG. 2B is a side view of the PCCC of FIG. 2A.

FIG. 2B is a side view of the case 200 in a closed position. Data connection ports 224 and 226 provide communication capabilities to the case 200. Ports 224 and 226 may be a mini universal serial bus (USB), micro universal USB port or an audio visual (NV) connector such as a high definition multimedia interface (HDMI) port and the like. Charging port 228 can be connected to the grid or other power source to feed the power source 212.

Figure 3:
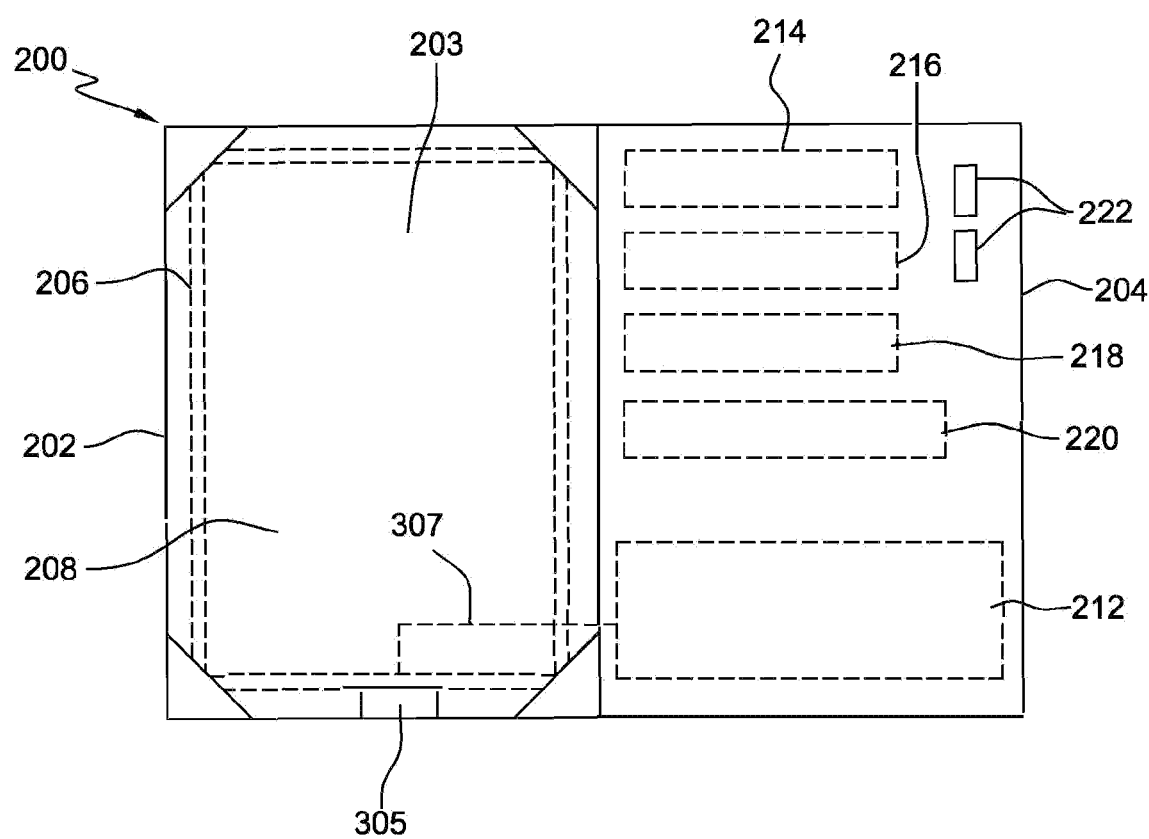
FIG. 3 is a front view of a second embodiment of the PCCC.

FIG. 3 is a second embodiment of the PCCC 200. Common numbering is used in FIGS. 3 though 9 and FIGS. 2A to 2B to denote similar elements. In this second embodiment, instead of wireless charging, a docking bay 305 having a set of electrical contacts is configured to electrically engage with the input/output contacts on a mobile communication device. The docking bay 305 may be a standard connector that allows the mobile communication device to receive power through line 307 from power source 217.

Figure 4:
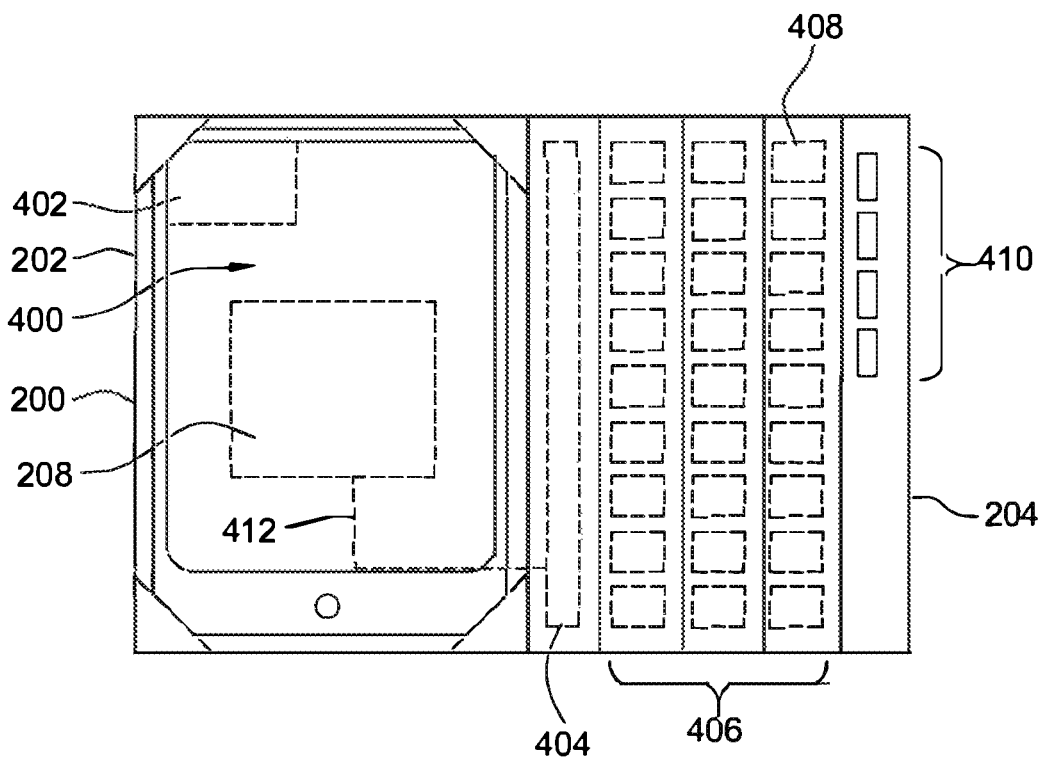
FIG. 4 is a front view of a third embodiment of the PCCC.

FIG. 4 illustrates a third embodiment of the PCCC 200. A mobile communication device 400 can be connected to a local area or wide area network through wireless modem 402 which may be 3G, 4G, 3G/4G, WHDMI, Bluetooth, WiFi, SuperWiFi, and other wireless standard. Module 404 is a replaceable, rechargeable battery that is charged through line 412 from the wireless charger 208 and receives power from mobile communication device 400. Module 404 performs the same function as power source 212 in FIG. 2 but is arranged differently in the case 200 as shown in FIG. 4. The wireless charger 208 may be located on the first panel 202 beneath the mobile communications device 400. The module 404 can also be charged from a power outlet when the case 200 is plugged in. The module 404 can be used as a power source for other modules (reference numerals 408 and 410 as discussed below) located in the case 200. An embedded memory bank 406 includes a plurality of memory modules and is mounted on the second panel 204. The memory bank modules may be 500 MegaByte (MB), 1 Gigabyte (GB), 1 Terabyte (TB) or the like in memory size. Memory slots 410 are capable of holding additional memory such as removable micro-Secure Digital (micro-SD) memory cards for storage expansion.

Figure 5:
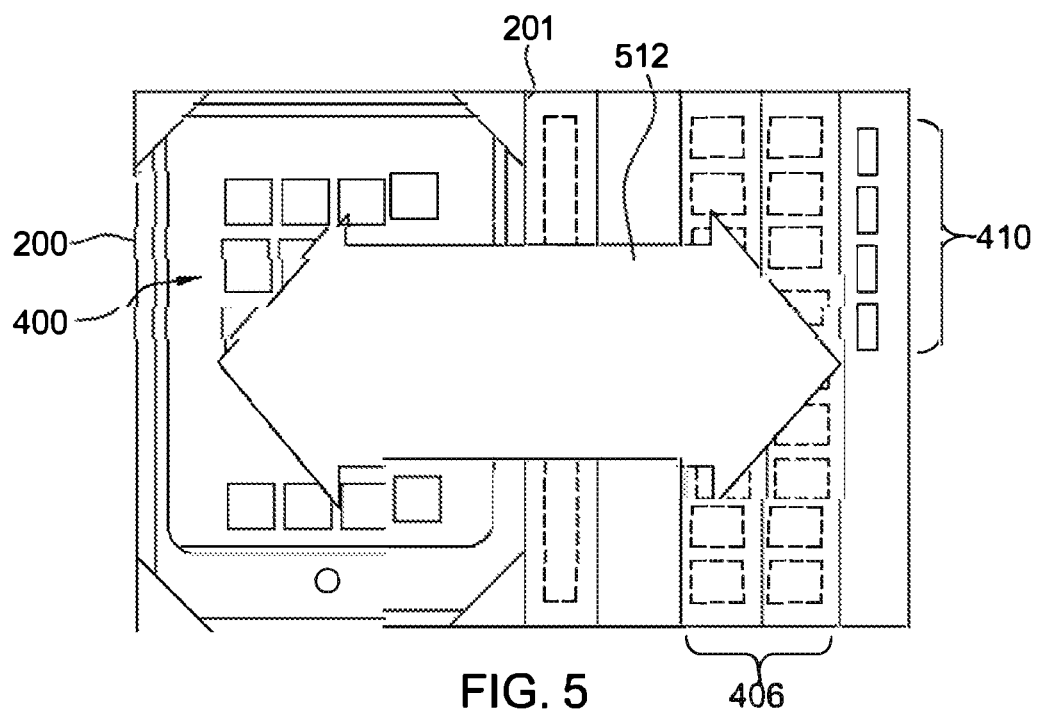
FIG. 5 is a front view of a fourth embodiment of the PCCC.

FIG. 5 illustrates a fourth embodiment of the PCCC 200 which demonstrates that the plurality of modules are detachable and could be two instead of three in the case 200. Also, FIG. 5 discloses a wireless data connection 512 between the device 400 and memory bank 406 using WiFi, SuperWiFi or Bluetooth protocols. In alternate embodiments, the data connection 512 could be a hardwired such as a Universal Serial Bus (USB), microUSB, miniUSB, or HDMI (with the data line being flexibly bendable across the flexible region 201 in the form of a ribbon cable or the like). In other embodiments, the connection could also be an optical wireless link or cable such as infrared. The data transfer could be bi-directional to allow for read and write both ways from device 400 to memory 406 and from memory 406 to device 400.

Figure 6A:
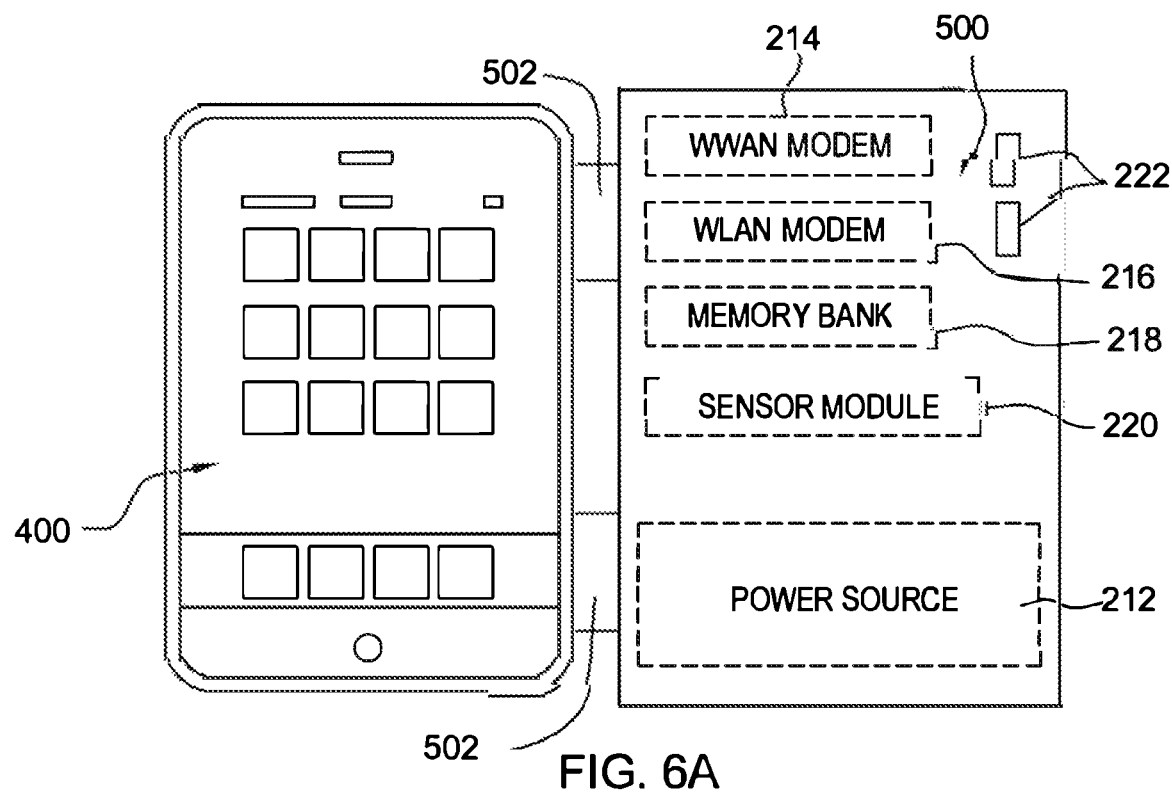
FIG. 6A is a front view of a fifth embodiment of the PCCC.
Figure 6B:
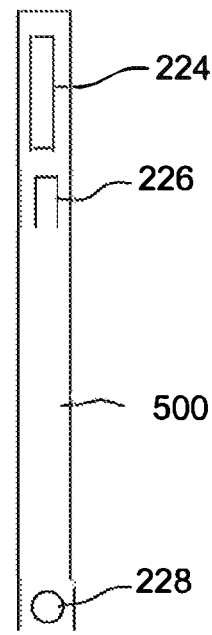
FIG. 6B is a side view of the PCCC of FIG. 6A.

FIG. 6A is another embodiment of the PCCC with just one panel 500 attached to the device 400 through attachments 502. Attachments 502 may be magnets, clip ins, connectors or some other type of hinge. The attachments 502 may internally include a plurality of electrical links to provide power from the power source 212 to the mobile communication device 400 as well as provide data communications between the modules on the panel 500 and the device 400. The power source 212 may include a wireless charging unit so as to wirelessly charge the device 400. The charging may take place when the panel 500 is in a lateral position relative to the device 400 as shown in FIG. 6A. In an alternative embodiment, the panel 500 may be folded over and placed in contact with the device 500 to establish an electrical power link between the power source 212 and electrical contacts located on the device 400. Also, similar to the embodiment of FIG. 5, a wireless data connection may be established between the device 400 and the plurality of modules on the panel 500 (items 214, 216, 218, 220, and 222). FIG. 6B is a side view of the panel 500 showing the connection ports 224, 226, and 228 which serve the same functions as described in connection with FIG. 2B above.

Figure 7:
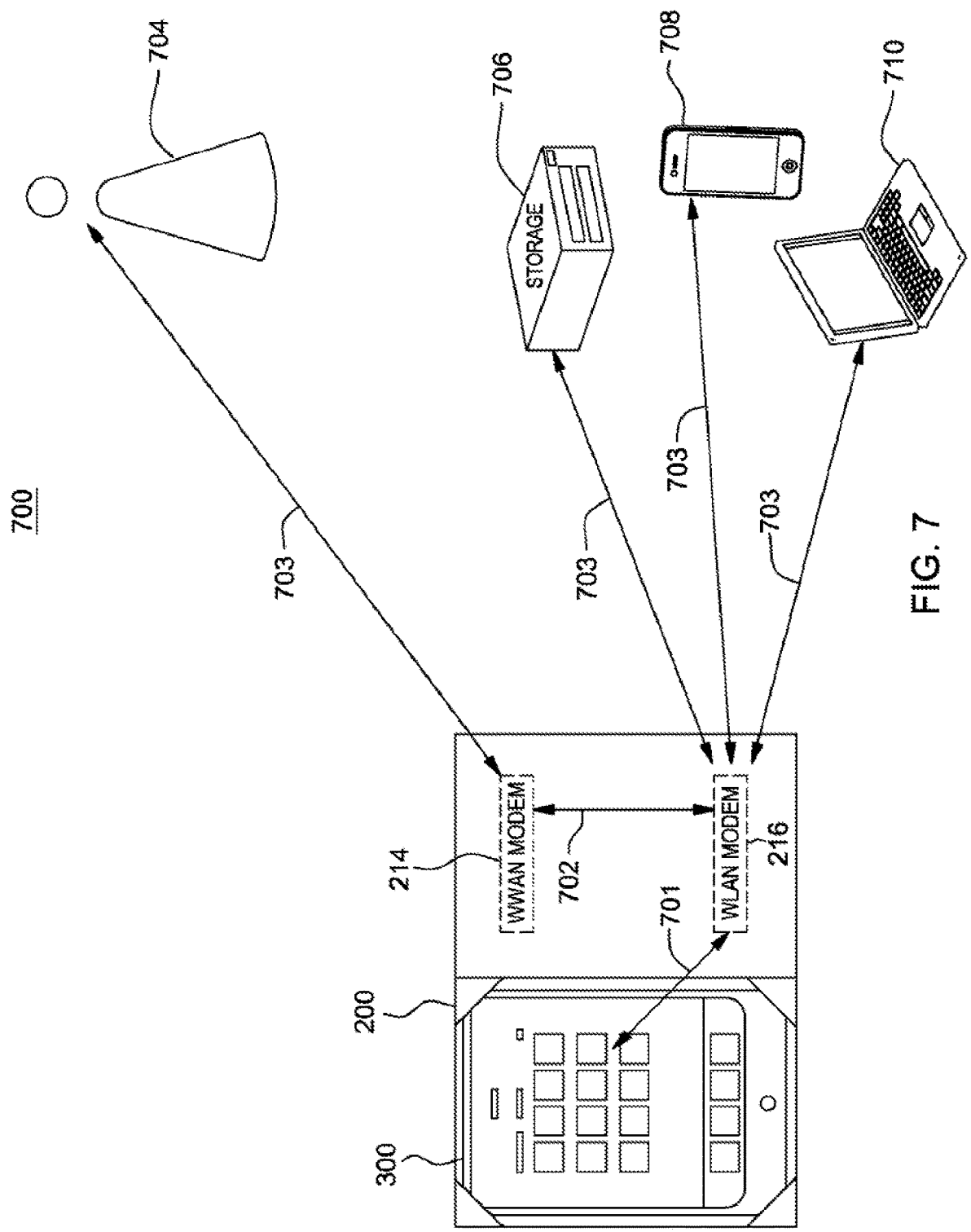
FIG. 7 is a schematic diagram of a PCCC in a cloud/networked environment utilizing 3G, 4G and similar wireless connections.

FIG. 7 illustrates the mobile communication device 300 and PCCC 200 operating in a cloud (or networked) environment 700. Storage 706, mobile phone 708 and personal computer (PC) 710 are part of the cloud upon which the mobile communications device 300 and PCCC 200 can exchange data and synchronize through a plurality of wireless links 703. The WWAN modem module 214 and the WLAN modem module 216 of FIG. 7 operate in a similar manner as described in connection with FIG. 2A above. The mobile computing device 300 communicates through a bi-directional wireless link 701 with the WLAN modem 216 using Bluetooth, WiFi, SuperWiFi and similar wireless standards. In another embodiment, the link 701 may be a wired link. WLAN modem 216 then can read and write wirelessly in a local environment with storage 706. The WLAN modem 216 can also communicate with another mobile phone 708 and PC 710. Alternatively, the mobile computing device 300 can communicate through WLAN 216 over a bi-directional link 702 with WWAN modem 214. WWAN modem 214 can communicate wirelessly using 3G/4G protocols over longer distances than the WLAN modem 216 with a cell tower 704 and then to the Internet. In the environment of FIG. 7, the case 200 is acting as "hotspot". As a hotspot, the case 200 offers network (e.g., Internet) access over the WWAN modem 214 or WLAN modem 216.

Figure 8:
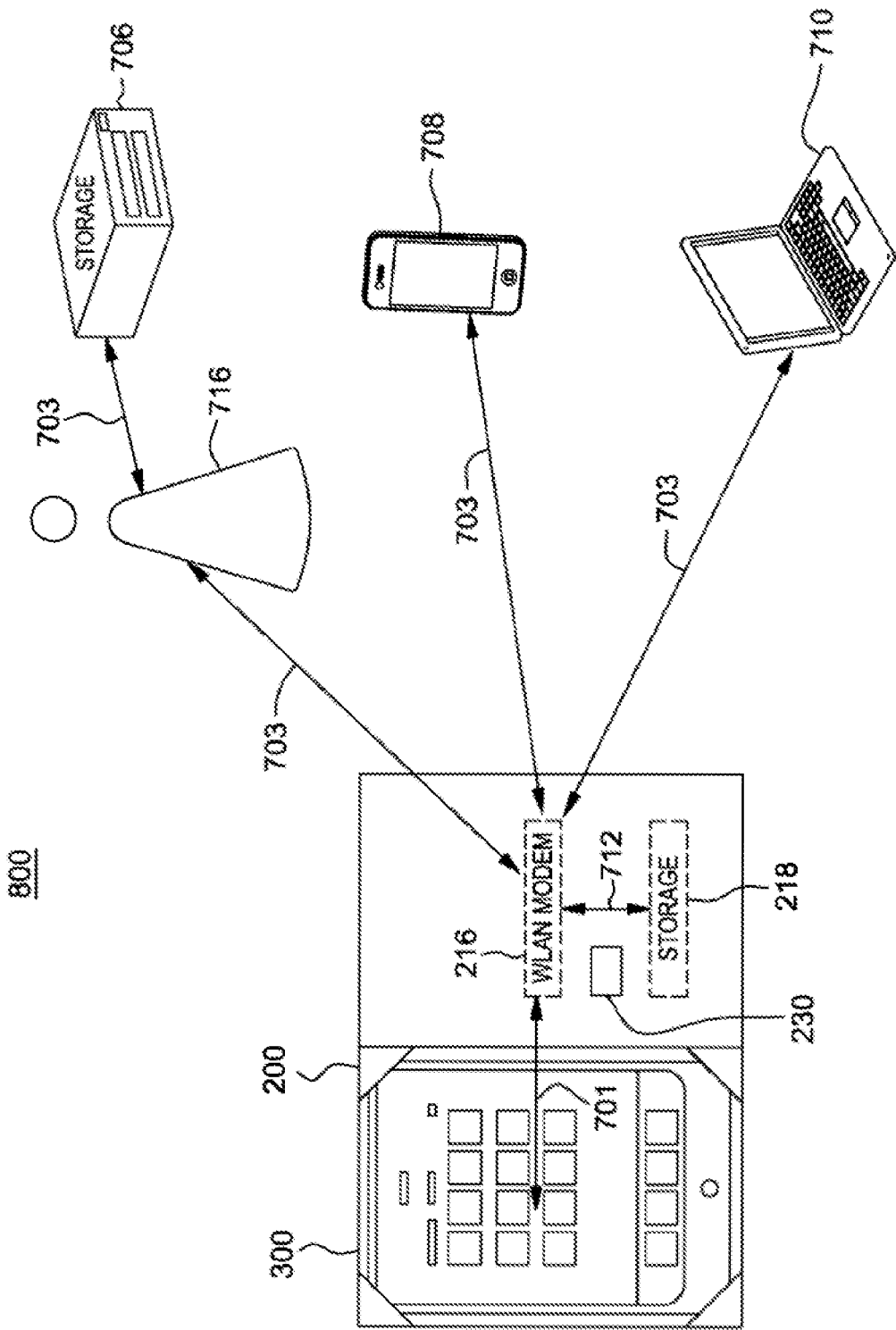
FIG. 8 is a schematic diagram of the PCCC in another cloud/networked environment system.

FIG. 8 illustrates another variation of the mobile communication device 300 and the case 200 in operation 800. This arrangement allows the local storage 218 to have access to a plurality of devices in the cloud such as the communication device 708, PC 710 and storage 706 through local wireless router (or access point) 716. As previously discussed in connection with FIG. 2A, sync input 230 can be operated when the mobile communication device is not present in the case 200 to backup all data contained in the components in the case 200 to the cloud (e.g., devices such as 706, 708, 710 and other devices). Another advantage is that this system allows for the formation of a "pass through Internet" from the mobile communication device 300 to devices 706, 708, 710 and a network (e.g., the Internet). WLAN modem 216 is connected to memory storage 218 through link 712 and is capable of establishing wireless communications with both the mobile communication device 300 and the devices 706, 708, and 710. In operation, the mobile communication device 300 establishes a wireless connection 701 through WiFi, SuperWiFi, 4G or the like to the WLAN modem 216. Through WLAN modem 216, the communication device 300 is capable of connecting to the memory storage 218 (e.g., providing information or instructions regarding reading and/or writing) while simultaneously browsing the Internet through wireless link 703 to access point 716. The term simultaneously as used herein shall mean immediate or nearly immediate succession in time. In another embodiment, the connection from the mobile communication device to the memory storage 218 could be wired. Alternatively, the communication device could be simultaneously connecting to memory storage 218 while communicating with devices 706,708 and 710 through wireless links 703. This pass through Internet feature allows the user to access data stored in the memory 218 and browse the Internet simultaneously from a single device (mobile communication device 300) or a plurality of devices. The WLAN modem 216 is designed to operate in one or more bands and cover one or more wireless standards. The bands may include first and second frequency bands (e.g., 2 GHz and 5 GHz). The WLAN modem 216 may use the first band for the transmission of information from memory storage 218 to the mobile communication device 300 and the second band for communications with the access point 716 (and thereby the Internet).

Figure 9:
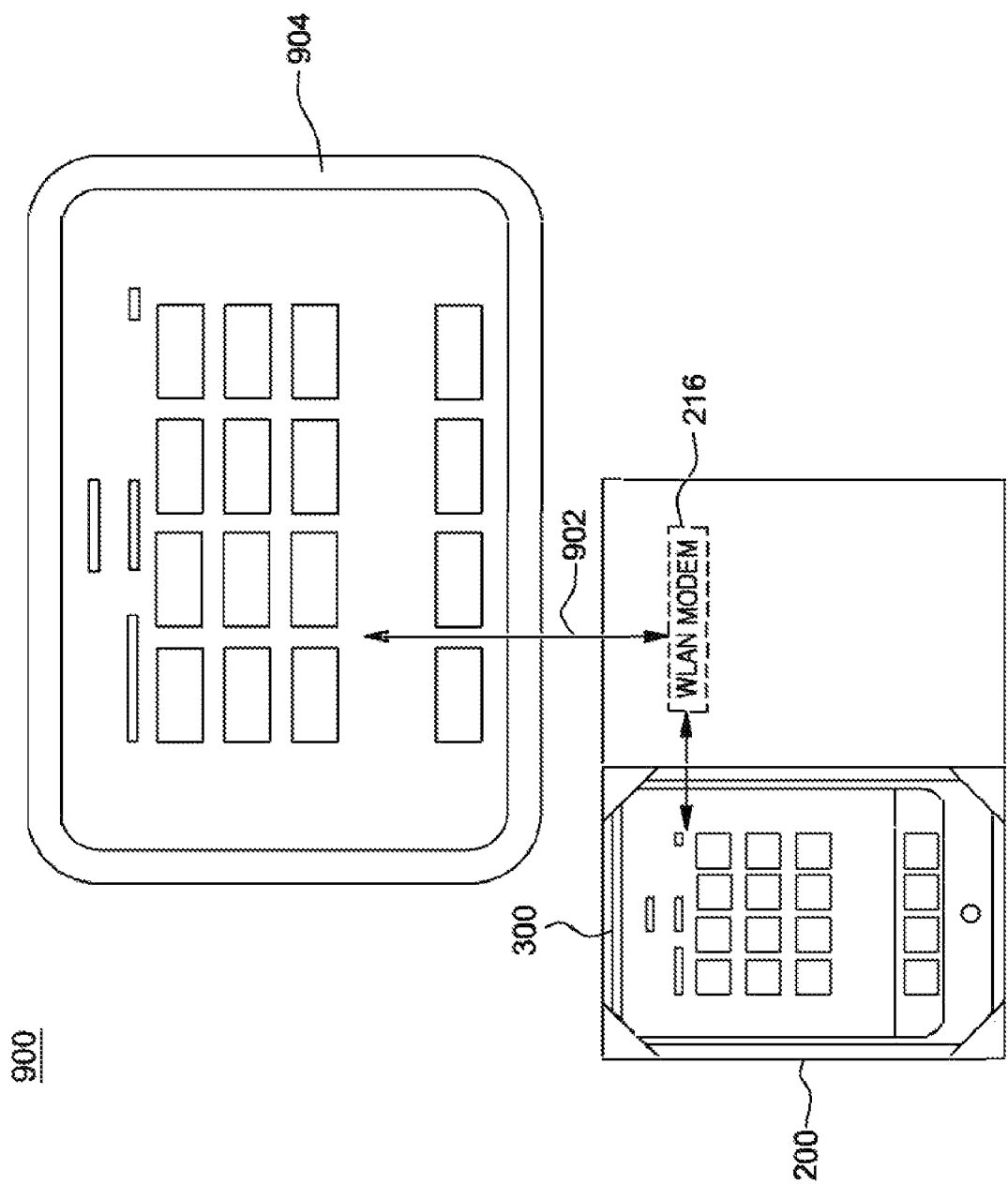
FIG. 9 is a view of the PCCC operating with a large external monitor.

FIG. 9 illustrates another environment 900 in which the PCCC 200 may operate. The PCCC 200 allows the mobile communication device 300 to link through WLAN 216 and wireless link 902 with large external monitor 904 using WiFi, SuperWiFi, WHDMI, or the like and display information (e.g., video, audio, or text) from either the mobile communication device 300, the memory storage or another source (e.g., devices 706, 708, 710) on to the monitor 904.

Figure 10:
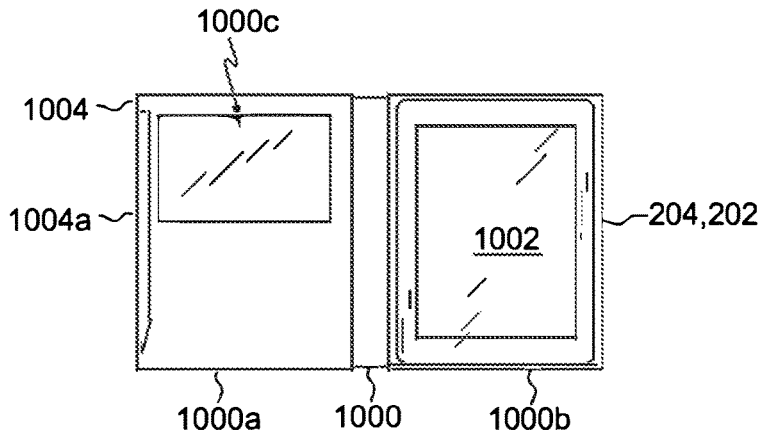
FIG. 10 is a front view of another embodiment 1000 of the PCCC which has a window in the left panel.

FIG. 10 is a front view of another embodiment 1000 of the PCCC which is shown in an open position. As previously discussed, the mobile computing device 1002 in the case 1000 could be an iPad®, iPhone®, PC tablet, Android® based tablet, TouchPad, Nexus 7®, Slate® or the like. Embodiment 1000 and embodiments 1100, 1200, 1300, 1400, 1700, 1800, 1900, 2000, 2100, 2200, and 2300 discussed below operate in a manner similar to the other embodiments of the PCCC disclosed above in the discussions of FIGS. 2A through 9. In embodiment 1000, however, the mobile computing device 1002 is mounted on the right (or second) panel 1000*b* of the case cover. Embodiment 1000 may provide a personal cloud to the user and access to wireless networks (such as 3G, 4G, WiFi, SuperWiFi, and similar wireless technologies). The right panel 1000*b* includes the electronic components, modules (including WLAN and WWAN wireless modules), memory and power source as described above with regard to second panel 204 in FIG. 2A. However, it is also includes the wireless charging module 208 which is shown FIG. 2A mounted on the first panel 202. So panel 100*b* includes the components of both 202 and 204 of FIG. 2A. In this embodiment 1000, the left (or first) panel 1000*a* of the case cover has a window 1000*c* which allows for a view of either all or part of the screen of the mobile device 1002 when the case is closed. For example, the window 1000*c* might be approximately one quarter to approximately one half the surface area of the left panel 1000*a*. The case 1000 also has an attachment 1004 for a stylus 1004*a* such as a pressure sensitive pen.

Figure 11:
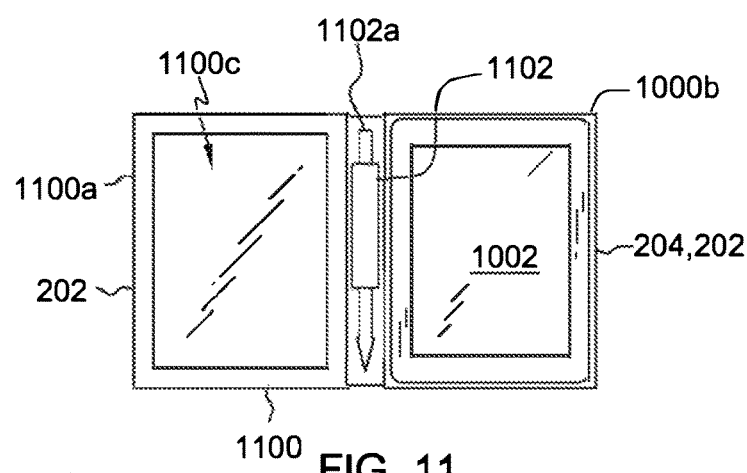
FIG. 11 illustrates an embodiment of the PCCC which has an embedded screen mounted on the left panel cover.

FIG. 11 illustrates an embodiment 1100 of the PCCC which has an embedded (or mounted) screen 1100*c* on the left (or first) panel cover 1100*a*. The mobile computing device 1002 is mounted on the right (or second) panel 1100*b*. Embodiment 1100 may provide a personal cloud to the user and access to wireless networks (such as 3G, 4G, WiFi, SuperWiFi, and similar wireless technologies). The right panel 1100*b* includes the electronic components, modules (including WLAN and WWAN wireless modules), memory and power source as described above with regard to second panel 204 in FIG. 2A. However, it is also may include the wireless charging module 208 which is shown FIG. 2A mounted on the first panel 202. In alternative embodiments, the wireless charging module 208 can be embedded in the left panel 1100a and provide power to the screen 1100c as shown in FIG. 2A mounted on the first panel 202. The screen of the mobile computing device 1002 and the screen 1100c each may be an organic light emitting diode (OLED), light emitting diode (LED), liquid crystal display (LCD), Mirasol®, E Ink or the like. The screen 1100c could have an embedded digitizer for drawing, writing and taking notes and be pen input sensitive. The embodiment 1100 has a holder (or attachment) 1102 for an input pen 1102a.

Figure 12:
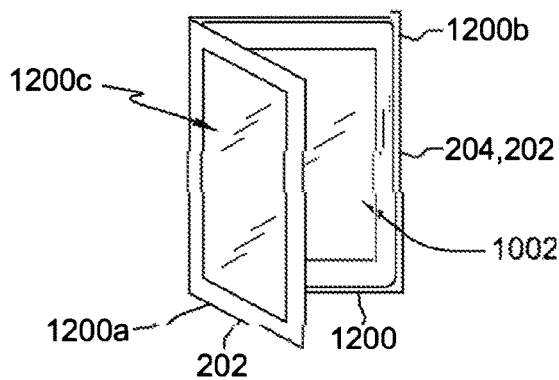
FIG. 12 illustrates an embodiment of the PCCC which has an embedded screen mounted on the outside of the left panel cover with the mobile device mounted in the right panel.
Figure 13:
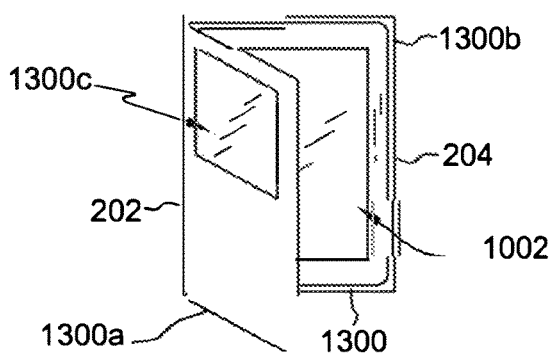
FIG. 13 shows a similar embodiment of the PCCC to that of FIG. 12 with an embedded screen also mounted on the outside of the left panel with the mobile device mounted on the right panel.

FIG. 12 illustrates an embodiment 1200 of the PCCC which has a screen 1200c (which may be embedded) mounted on the outside of the left panel cover 1200a with the mobile device 1002 located in the right panel 1200b. FIG. 13 shows a similar embodiment 1300 of the PCCC with an embedded screen 1300c also mounted on the outside of the left panel 1300a with the mobile device 1002 mounted on the right panel 1300b. However in this embodiment, the screen 1300c covers approximately twenty-five percent to approximately half the surface of the left panel 1300a. The right panels 1200b and 1300b includes the electronic components, modules (including WLAN and WWAN wireless modules), memory and power source as described above with regard to second panel 204 in FIG. 2A. However, the panels 1200b and 1300b may also include the wireless charging module 208 which is shown in FIG. 2A mounted on the first panel 202. In an alternative embodiment, the wireless charging module 208 can be embedded in the left panels 1200a and 1300a and provide power to the screens 1200c and 1300c as shown in FIG. 2A with regard to first panel 202. The screen of the mobile computing device 1002 and the screens 1200c and 1300c each may be an OLED, LED, LCD, Mirasol®, E Ink or the like. The screen 1200c and 1300c could have an embedded digitizer for drawing, writing and taking notes and be pen input sensitive.

Figure 14:
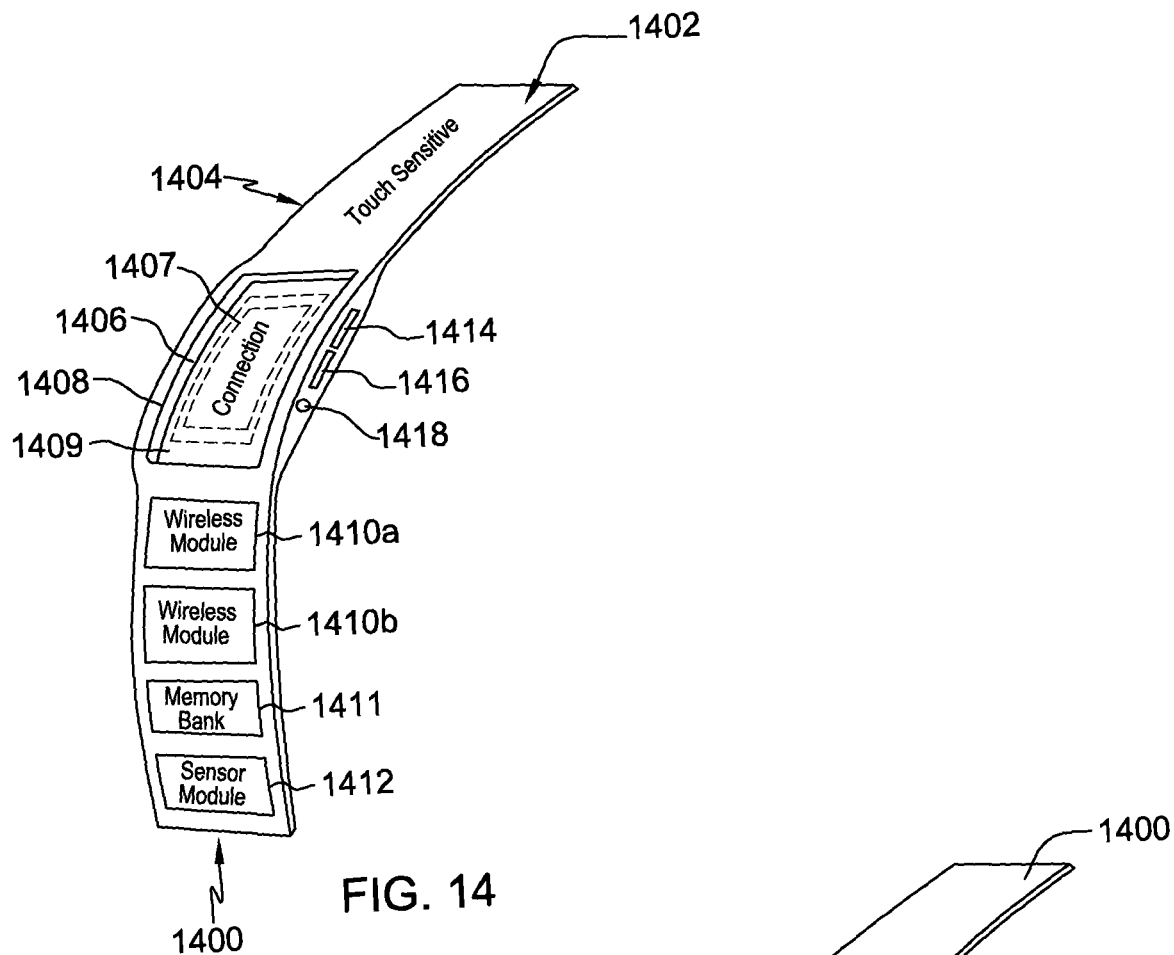
FIG. 14 illustrates an embodiment which operates in a manner similar to the other embodiments of the PCCC disclosed above in the discussions of FIGS. 2A-13 but instead the electronic components are mounted on a structure such as a band instead of a case.

FIG. 14 is a view of another embodiment 1400 of the PCCC. Embodiment 1400 operates in a manner similar to the other embodiments of the PCCC disclosed above in the discussions of FIGS. 2A-13 but instead the electronic components are mounted on a structure such as a band instead of a case. Embodiment 1400 provides a personal cloud to the user and access to wireless networks (such as 3G, 4G, WiFi, SuperWiFi, and similar wireless technologies). The structure 1400 may be a watch-type band made of waterproof material and manufactured by injection molding. Electronics components in the band such as controllers, memory modules, batteries, and the like may be entirely covered by the structural material. In alternative embodiments the structure 1400 may be made of any material (hard and/or soft) that makes the embodiment 1400 lightweight but durable and resilient such as plastic, silicone, ceramic, fabric, leather, steel, aluminum, fiberglass, titanium, Kevlar, and/or rubber. The surface of the structure itself may be touch sensitive 1402 to communicate with a mobile device located on the band in cavity 1406 or nearby. The band may be substantially circular or substantially oblong in shape and be capable of being wrapped around the hand, wrist, forearm, bicep, head, or leg of the wearer or around the wearers' clothing such as a hat (or helmet). The band should have some type of clasping device (e.g., Velcro, metal clasp, etc.) mounted on each of the ends of the band for attachment. A cavity 1406 is located in the band and, typically, in the central portion of the band. Wireless charging circuitry 1404 may be in electrical connection with cavity 1406 and may extend out from both sides of cavity 1406. The wireless charging circuitry can provide both power and serve as a data link. For example, the wireless charging circuitry 1404 may be connected to the touch sensitive surface 1402 to communicate data to the mobile device in the cavity 1406. The wireless charging circuitry 1404 may be ribbon cable so that it flexibly bends with the band. Wireless charging circuitry 1404 may be internal to the band and extend along substantially the length of the band. The wireless charging circuitry 1404 may be connected to electronic modules and components mounted on the band such as modules 1410 and 1412 and memory bank module 1411 (which may be made up of a plurality of memory modules). The wireless charging circuitry 1404 is configured to transfer power from at least one, several or all of the of the modules to a mobile computing device mounted in the cavity 1406 or may transfer power from the mobile computing device in the cavity to at least one, several or all of the modules 1410, 1411, and 1412. Similar to synchronization button 230, the band may also have an input (such as the touch sensitive screen 1404) configured to direct the plurality of electronic components to receive synchronization information from a wireless network.

Cavity 1406 contains antenna 1407 which may be mounted on a miniature wireless charging unit 1408 or mounted separately. Wireless charging unit 1408 is connected to wireless charging circuitry 1404 and may operate by magnetic resonance, inductive charging, or power over RF or similar wireless charging methods to charge an a mobile communication device mounted in the cavity 1406. Along with the wireless charging unit 1408 there may be a battery 1409 located in the cavity and in connection with the wireless charging unit 1408 and the wireless charging circuitry 1404. Reference numerals 1414 and 1416 indicate data ports providing outside connections to cavity 1406. Data ports 1414 and 1416 may be microUSB, HDMI, A/V inputs or the like and are linked to both the mobile communication device in the cavity 1406 and over wireless charging circuitry 1404 to the modules 1410a, 1410b, 1411, and 1412. Port 1418 may be a charging port to provide power to the wireless charging unit 1408 and/or battery 1409 located in the cavity 1406 and ultimately to the mobile communication device and the electronic components in the band. Electrically connected to the cavity 1406 is a wireless modules 1410a and 1410b. Wireless module 1410a may be a WWAN modem to link the electronic device to 3G, 4G or other future network. Wireless module 1410b may be a WLAN modem to link the electronic device using WiFi, SuperWiFi, Bluetooth, WHDMI, or the like. Functionally modules 1410a and 1410b operate similarly to modules 214 and 216 as described above. Memory bank 1411 (similar to memory bank 218) may include a plurality of replaceable memory modules having internal storage such as SSD, flash memory, or the like. Since the memory bank 1411 (and its memory modules) are coupled (or in communication) with the wireless modems 1410a and 1410b, the band is therefore configured to allow for simultaneous connection of the mobile communication device with the memory bank 1411 and through the wireless modem to a network. Module 1412 (similar to module 220) may be a sensory module and may contain a sensor chip which can detect biometric inputs such as finger prints, eye movement, face shape and the like.

Figure 15:
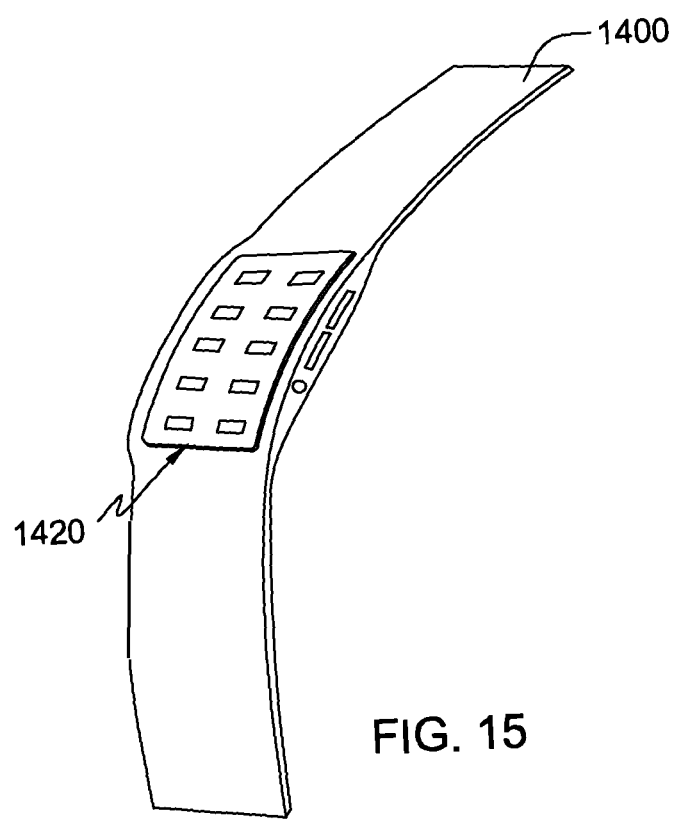

FIG. 15 shows detachably mounted on the structure 1400 a mobile wireless computing device 1420 which functions like (and may actually be) an iPad®, iPhone®, PC tablet, Android® based tablet, TouchPad, Nexus 7®, Slate® or the like. Cavity 1406 may be designed to allow the mobile computing device 1420 to be snapped into position in the cavity 1406. The form factor of the mobile computing device 1420 can be the typical size of these devices and be mounted substantially lengthwise with the band or substantially perpendicular to the direction of the band. The form factor of the computing device 1420 can also be approximately the size of a watch or a watch phone having a rectangular or square shape with outside dimensions such as: length in the range of 22 mm to 44 mm; width in the range of 22 mm to 44 mm; and height (or thickness) in the range of 4 mm to 18 mm. The screen sizes of these computing devices can also be rectangular or square and be in the ranges such as: length 18 mm to 42 mm; width in the range of 18 mm to 42 mm; and height (or thickness) in range of 2 mm to 4 mm. In the case of substantially circular profiles the dimensions may be: diameter in the range of 22 to 44 mm and height (or thickness) in the range of 4 mm to 18 mm with substantially circular screens having dimensions of: 18 mm to 42 mm and height (or thickness) 2 mm to 4 mm. Further, the mobile computing device 1420 can be flexible. The device 1420 can be mounted in or on top of the cavity 1406 using a mechanical attachment (e.g., snap-in) or a magnetic coupling. In addition, as shown in FIG. 15, the modules 1410*a*, 1410*b*, 1411, and 1012 may be integrated into the structure of the band and therefore not visible from the outside of the band.

Figure 16:
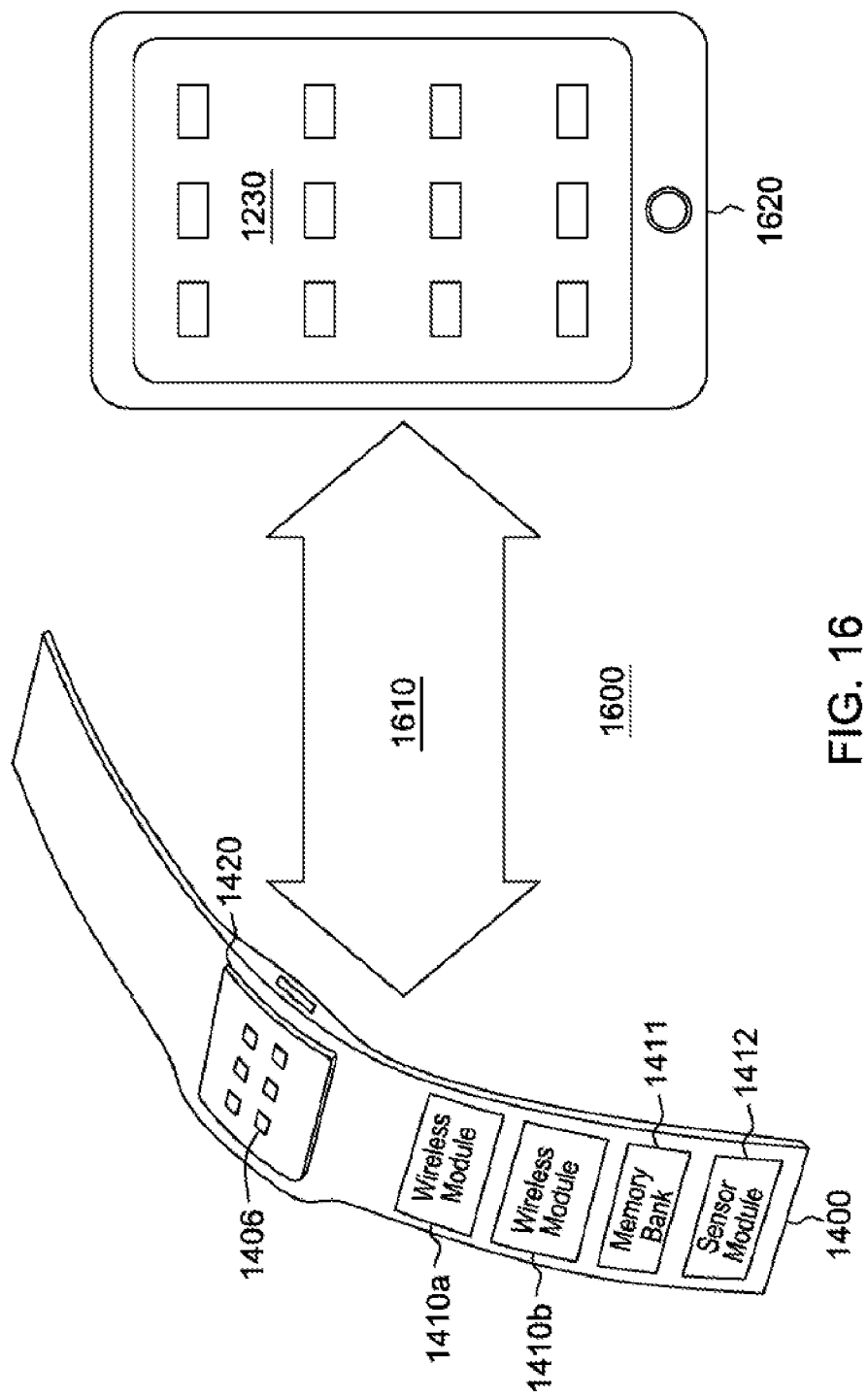
FIG. 16 illustrates the embodiment of FIG. 14 operating in a cloud environment allowing the mobile communication device to link to an external device.

FIG. 16 illustrates the embodiment 1400 operating in a cloud environment 1600. The embodiment 1400 allows mobile communication device 1420 to communicate with an external device 1620. The mobile computing device 1420 can connect directly through a wireless link 1610 or a wired connection (not shown). The mobile computing device 1420 can also link through the wireless modules 1410*a* and 1410*b* (e.g., a WLAN module, a WWAN module) and the wireless link 1610 to the external device 1620. The wireless link 1610 may be made using WiFi, SuperWiFi, WHDMI, Bluetooth, NFC type protocols, 3G/4G, or the like. The external device 1620 can be almost any type of display device such as an iPad®, iPhone®, PC tablet, Android® based tablet, TouchPad, Nexus 7®, Slate®, smart TV, display for a projection device or the like. The band system described herein allows a user of the band to easily display information stored in the memory bank 1411 on the band to an external device 1620. Therefore, the operator of the band does not have to carry around a large display but rather can mate (usually wirelessly) with almost any type of much larger display to share information stored in the memory banks of the band including text, audio and video materials. In alternative embodiments, the computing device may not have a screen at all and the band may be designed to provide the functionalities of a mobile computing device but without a display screen at all. The band (whether there is a mobile computing device mounted therein or not) is configured to mate with whichever display is readily available. Embodiments 1100, 1200, 1300, 1700, 1800, 1900, 2000, 2100, 2200, and 2300 discussed herein are also configured to mate with an external device.

FIG. 17 illustrates an embodiment 1700 of the PCCC which has a screen 1700*b* mounted on a structure such as band 1700*a*. Examples of the band 1700*a* include a bracelet or sweatband. The screen 1700*b* may be flexible and cover less than the entire band in a range approximately 25% to 50% of the band or 50% to 75% of the band. The screen 1700*b* may be an OLED, LED, LCD, Mirasol®, E Ink or the like. In alternative embodiments, the screen 1700*b* may include an embedded digitizer for drawing, writing and taking notes and be pen input sensitive. Embodiment 1700 provides a personal cloud to the user and access to wireless networks (such as 3G, 4G, WiFi, SuperWiFi, and similar wireless technologies). The structure 1700 may be a band 1700*a* made of waterproof material and manufactured by injection molding. Electronics components in the band such as controllers, memory modules, batteries, and the like may be entirely covered by the structural material. The band 1700*a* may include the electronic components, modules (including WLAN and WWAN wireless modules), memory and power source as described above with regard to second panel 204 in FIG. 2A. However, it is also may include the wireless charging module 208 which is shown FIG. 2A mounted on the first panel 202. In alternative embodiments the structure 1700 may be made of any material (hard and/or soft) that makes the embodiment 1700 lightweight but durable and resilient such as plastic, silicone, ceramic, fabric, leather, steel, aluminum, fiberglass, titanium, Kevlar, and/or rubber. The band 1700*a* may be substantially circular or substantially oblong in shape and be capable of being wrapped around the hand, wrist, forearm, bicep, head, or leg of the wearer or around the wearers' clothing such as a hat (or helmet). The band may have some type of clasping device (e.g., Velcro, metal clasp, etc.) mounted on each of the ends of the band for attachment. Wireless charging circuitry may extend out from both sides of screen 1700*b*. The wireless charging circuitry can provide both power and serve as a data link. The wireless charging circuitry may be ribbon cable so that it flexibly bends with the band. Wireless charging circuitry may be internal to the band 1700*a* and extend along substantially the length of the band. The wireless charging circuitry may be wireless and have memory modules. The wireless charging circuitry may be configured to transfer power from at least one, several or all of the of the modules to screen 1700*b* (or an attached mobile computing device) or may transfer power from the screen 1700*b* (or an attached mobile computing device) to at least one, several or all of the modules. Similar to synchronization button 230, the band may also have an input configured to direct the plurality of electronic components to receive synchronization information from a wireless network. The band 1700*a* may contain an antenna. A wireless charging unit may be connected to the wireless charging circuitry and may operate by magnetic resonance, inductive charging, or power over RF or similar wireless charging methods to charge the screen 1700*b* or a nearby mobile computing device. Along with the wireless charging unit there may be a battery located in the band 1700*a* and in connection with the wireless charging unit and the wireless charging circuitry. The band 1700*a* may include data ports providing outside connections to the band 1700*a* and screen 1700*b*. The data ports may be microUSB, HDMI, A/V inputs or the like and are linked to both the screen 1700*b* and over wireless charging circuitry to the modules. One port may be a charging port to provide power to the wireless charging unit and/or a battery and ultimately to the screen 1700*b* and the electronic components in the band 1700*a*. Electrically connected to the screen 1700*b* may be a plurality of wireless modules. One wireless module may be a WWAN modem to link the electronic device to 3G, 4G or other future network. Alternatively or additionally, another wireless module may be a WLAN modem to link the electronic device using WiFi, SuperWiFi, Bluetooth, WHDMI, or the like. Functionally these wireless modules will operate similarly to modules 214 and 216 as described above. A memory bank (similar to memory bank 218) may include a plurality of replaceable memory modules having internal storage such as SSD, flash memory, or the like. Since the memory bank (and its memory modules) may be in communication with the wireless modems, the band is therefore configured to allow for simultaneous connection of the mobile communication device with the memory bank and through the wireless modem to an external network. There may also be a module (similar to module 220) that may be sensory module and may contain a sensor chip which can detect biometric inputs such as finger prints, eye movement, face shape and the like.

FIGS. 18A and 18B illustrate an embodiment 1800 of the PCCC which has a wallet structure which is similar in structure (albeit smaller) to the case 200 as shown in FIG. 2A with a first wallet panel 1800*a* and a second wallet panel 1800*b*. As shown in FIG. 18A, screen 1800*c* may be embedded or mounted on the outside of the first wallet panel 1800. The screen 1800*c* may be flexible and cover in a range between either approximately half the entire surface or the approximately the entire surface of first wallet panel 1800*a*. The screen 1800*c* may be an OLED, LED, LCD, Mirasol®, E Ink or the like. The screen 1800*c* could have an embedded digitizer for drawing, writing and taking notes and be pen input sensitive. FIG. 18B shows the wallet 1800 in an open position. As discussed with regard to previous embodiments above, wallet 1800 provides a personal cloud to the user and access to wireless networks (such as 3G, 4G, WiFi, SuperWiFi, and similar wireless technologies). The wallet 1800 may include the electronic components, modules (including WLAN and WWAN wireless modules), memory and power source as described above with regard to second panel 204 in FIG. 2A. However, it is also may include the wireless charging module 208 which is shown FIG. 2A mounted on the first panel 202. Electronics components in the wallet 1800 such as controllers, memory modules, batteries, and the like may be entirely covered by the structural material. The structure 1800 may be made of leather and/or waterproof material. In alternative embodiments the structure 1800 may be made of any material (hard and/or soft) that makes the embodiment 1800 lightweight but durable and resilient such as plastic, silicone, ceramic, fabric, leather, steel, aluminum, fiberglass, titanium, Kevlar, and/or rubber. The wallet 1800 may be approximately rectangular in shape. Wireless charging circuitry may extend out from the screen 1800*c*. The wireless charging circuitry can provide both power and serve as a data link. The wireless charging circuitry may be ribbon cable so that it flexibly bends with the wallet. Wireless charging circuitry may be internal to the wallet and extend along substantially the length of the wallet in both the first panel 1800*a* and the second panel 1800*b*. The wireless charging circuitry may operate wirelessly and have a plurality of modules. The wireless charging circuitry may be configured to transfer power from at least one, several or all of the of the modules to screen 1800*c* or may transfer power from the screen 1800*c* to at least one, several or all of the modules. The wireless charging circuitry may also attach (e.g., through a USB port) to a mobile computing device to provide power to or receive power from the mobile computing device. Similar to synchronization button 230, the wallet 1800 may also have an input configured to direct the plurality of electronic components to receive synchronization information from a wireless network. The wallet 1800 may further contain an antenna. A wireless charging unit may be connected to wireless charging circuitry and may operate by magnetic resonance, inductive charging, or power over RF or similar wireless charging methods to charge the screen 1800*c* or provide power to or receive power from a nearby mobile computing device and/or modules (e.g., power modules) in the wallet 1800. Along with the wireless charging unit there may be a battery located in the wallet 1800 and in connection with the wireless charging unit and the wireless charging circuitry. The wallet 1800 may include data ports providing outside connections to the wallet 1800 and screen 1800*c*. The data ports may be microUSB, HDMI, NV inputs or the like and are linked to both the screen 1800*c* and over wireless charging circuitry to the modules. One port may be a charging port to provide power to the wireless charging unit, a battery, screen 1800*c*, the electronic components in the wallet 1800 and/or an attached (or detached) mobile computing device. Electrically connected to the screen 1800*c* may be wireless modules. One wireless module may be a WWAN modem to link the electronic device to 3G, 4G or other future network. Alternatively or additionally, another wireless module may be a WLAN modem to link the electronic device using WiFi, SuperWiFi, Bluetooth, WHDMI, or the like. Functionally these wireless modules will operate similarly to modules 214 and 216 as described above. A memory bank (similar to memory bank 218) may include a plurality of replaceable memory modules having internal storage such as SSD, flash memory, or the like. Since the memory bank (and its memory modules) may be communication with the wireless modems, the wallet 1800 is therefore configured to allow for simultaneous connection of the mobile communication device with the memory bank and through the wireless modem to a network. There may also be a module (similar to module 220) which may be a sensory module and may contain a sensor chip which can detect biometric inputs such as finger prints, eye movement, face shape and the like.

FIGS. 19A and 19B illustrate an embodiment 1900 of the PCCC which also has a wallet structure with a first wallet panel 1900*a* and a second wallet panel 1900*b*. Embodiment 1900 is constructed and functions in the same manner as embodiment 1800 except for the absence of a screen.

Figure 20A:
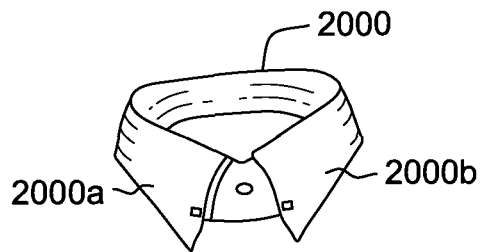
FIGS. 20A and 20B illustrate an embodiment of the PCCC which has a collar shape.
Figure 20B:
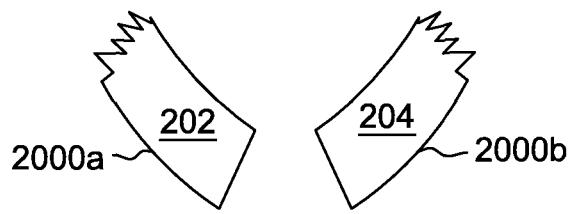

FIGS. 20A and 20B illustrate an embodiment 2000 of the PCCC which has a collar structure with a first collar panel 2000*a* and a second collar panel 2000*b*. As discussed with regard to previous embodiments above, collar 2000 provides a personal cloud to the user and access to wireless networks (such as 3G, 4G, WiFi, SuperWiFi, and similar wireless technologies). The structure 2000 may be made of clothe and/or waterproof material. The collar 2000 may include the electronic components, modules (including WLAN and WWAN wireless modules), memory and power source as described above with regard to second panel 204 in FIG. 2A. However, it is also may include the wireless charging module 208 which is shown FIG. 2A mounted on the first panel 202. Electronics components in the collar 2000 such as controllers, memory modules, batteries, and the like may be entirely covered by the structural material. In alternative embodiments the structure 2000 may be made of any material (hard and/or soft) that makes the embodiment 2000 lightweight but durable and resilient such as plastic, silicone, ceramic, fabric, leather, steel, aluminum, fiberglass, titanium, Kevlar, and/or rubber. The collar 2000 may be rectangular or trapezoidal in shape. Wireless charging circuitry may extend throughout the first collar panel 2000*a* and second collar panel 2000*b*. The wireless charging circuitry can provide both power and serve as a data link. The wireless charging circuitry may be ribbon cable so that it flexibly bends with the collar. Wireless charging circuitry may be internal to the collar and extend along substantially the length of the collar in both the first panel 2000*a* and the second panel 2000*b* and electrically connect the two panels. The wireless charging circuitry may be wireless and have a plurality of modules. The wireless charging circuitry may be configured to transfer power from at least one, several or all of the of the modules. A mobile wireless device may be configured to attach to the collar 2000 and receive power from or provide power to the wireless charging circuitry.

Similar to synchronization button 230, the collar 2000 may also have an input configured to direct the plurality of electronic components to receive synchronization information from a wireless network. The collar 2000 may further contain an antenna. A wireless charging unit may be connected to wireless charging circuitry and may operate by magnetic resonance, inductive charging, or power over RF or similar wireless charging methods to provide power to or receive power from a mobile computing device and/or the modules (e.g., power modules) in the collar 2000. Along with the wireless charging unit there may be a battery located in the collar 2000 and in connection with the wireless charging unit and the wireless charging circuitry. The collar 2000 may include data ports providing outside connections to the collar 2000. The data ports may be microUSB, HDMI, A/V inputs or the like and are linked wireless charging circuitry to the modules. One port may be a charging port to provide power to the wireless charging unit, a battery, the electronic components in the collar 2000 and/or an attached (or nearby detached) mobile computing device. The collar 2000 may include a wireless module which may be a WWAN modem to link the electronic device to 3G, 4G or other future network. Alternatively or additionally, another wireless module may be a WLAN modem to link the electronic device using WiFi, SuperWiFi, Bluetooth, WHDMI, or the like. Functionally these wireless modules will operate similarly to modules 214 and 216 as described above. A memory bank (similar to memory bank 218) may include a plurality of replaceable memory modules having internal storage such as SSD, flash memory, or the like. Since the memory bank (and its memory modules) may be communication with the wireless modems, the band is therefore configured to allow for simultaneous connection of the mobile communication device with the memory bank and through the wireless modem to a network. There may also be a module (similar to module 220) may be sensory module and may contain a sensor chip which can detect biometric inputs such as finger prints, eye movement, face shape and the like.

Figure 21A:
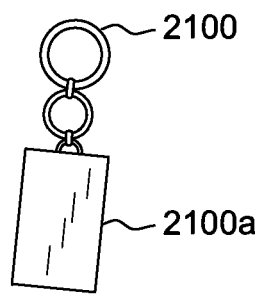
FIGS. 21A and 21B illustrate an embodiment of the PCCC which has a key chain shape.
Figure 21B:
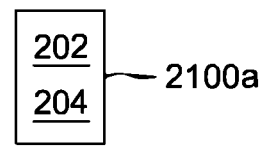

FIG. 21 illustrates an embodiment 2100 of the PCCC which has a key chain (or fob) shape with a key chain panel 2100a. As discussed with regard to previous embodiments above, key chain 2100 provides a personal cloud to the user and access to wireless networks (such as 3G, 4G, WiFi, SuperWiFi, and similar wireless technologies). The structure 2100 may include the electronic components, modules (including WLAN and WWAN wireless modules), memory and power source as described above with regard to second panel 204 in FIG. 2A. However, it is also may include the wireless charging module 208 which is shown FIG. 2A mounted on the first panel 202. Electronics components in the band such as controllers, memory modules, batteries, and the like may be entirely covered by the structural material. The structure 2100 may be made of waterproof material. In alternative embodiments the structure 2100 may be made of any material (hard and/or soft) that makes the embodiment 2100 lightweight but durable and resilient such as plastic, silicone, ceramic, fabric, leather, steel, aluminum, fiberglass, titanium, Kevlar, and/or rubber. The key chain 2100 may be substantially rectangular, substantially cubic or substantially circular in shape. Wireless charging circuitry may extend throughout the key chain panel 2100a. The wireless charging circuitry can provide both power and serve as a data link. The wireless charging circuitry may be a ribbon cable. Wireless charging circuitry may be internal to the key chain 2100 and extend along substantially the length of the key chain panel 2100a. The wireless charging circuitry may be wireless and have a plurality of modules. The wireless charging circuitry may be configured to transfer power from at least one, several or all of the modules. A mobile wireless device may be configured to attach to the key chain panel 2100a and receive from or provide power to the wireless charging circuitry. Similar to synchronization button 230, the key chain 2100 may also have an input configured to direct the plurality of electronic components to receive synchronization information from a wireless network. The key chain 2100 may further include an antenna. A wireless charging unit may be connected to wireless charging circuitry and may operate by magnetic resonance, inductive charging, or power over RF or similar wireless charging methods to provide power to or receive power from a nearby mobile device and/or modules (e.g., power modules) in the key chain 2100. Along with the wireless charging unit there may be a battery located in the key chain 2100 and in connection with the wireless charging unit and the wireless charging circuitry. The key chain may include data ports providing outside connections to the key chain 2100. The data ports may be microUSB, HDMI, A/V inputs or the like and are linked wireless charging circuitry to the modules. One port may be a charging port to provide power to the wireless charging unit, a battery, the electronic components in the key chain 2100 and/or an attached (or nearby non-attached) mobile device. The key chain 2100 may include a wireless module which may be a WWAN modem to link the electronic device to 3G, 4G or other future network. Alternatively or additionally, another wireless module may be a WLAN modem to link the electronic device using WiFi, SuperWiFi, Bluetooth, WHDMI, or the like. Functionally these wireless modules will operate similarly to modules 214 and 216 as described above. A memory bank (similar to memory bank 218) may include a plurality of replaceable memory modules having internal storage such as SSD, flash memory, or the like. Since the memory bank (and its memory modules) may be communication with the wireless modems, the band is therefore configured to allow for simultaneous connection of the mobile computing device with the memory bank and through the wireless modem to a network. There may also be a module (similar to module 220) may be sensory module and may contain a sensor chip which can detect biometric inputs such as finger prints, eye movement, face shape and the like.

Figure 22A:
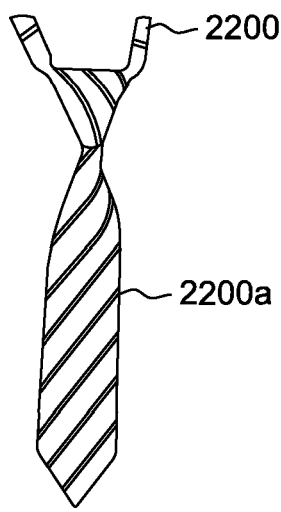
FIGS. 22A and 22*b* illustrate an embodiment of the PCCC which has a tie shape.
Figure 22B:
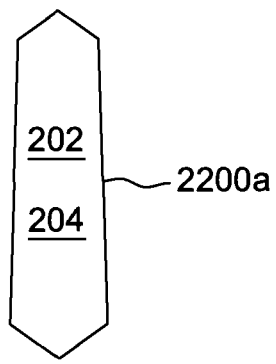

FIG. 22 illustrates an embodiment 2200 of the PCCC which has a tie shape structure with a tie panel 2200a. As discussed with regard to previous embodiments above, tie 2200 provides a personal cloud to the user and access to wireless networks (such as 3G, 4G, WiFi, SuperWiFi, and similar wireless technologies). The structure 2200 may include the electronic components, modules (including WLAN and WWAN wireless modules), memory and power source as described above with regard to second panel 204 in FIG. 2A. However, it is also may include the wireless charging module 208 which is shown FIG. 2A mounted on the first panel 202. Electronics components in the tie such as controllers, memory modules, batteries, and the like may be entirely covered by the structural material. The structure 2200 may be made of cloth and/or waterproof material. In alternative embodiments the structure 2200 may be made of any material (hard and/or soft) that makes the embodiment 2200 lightweight but durable and resilient such as plastic, silicone, ceramic, fabric, leather, steel, aluminum, fiberglass, titanium, Kevlar, and/or rubber. Wireless charging circuitry may extend throughout the tie panel 2200a. The wireless charging circuitry can provide both power and serve as a data link. The wireless charging circuitry may be a flexible, ribbon cable. Wireless charging circuitry may be internal to the tie 2200 and extend along substantially the length of the tie panel 2200a. The wireless charging circuitry may be wireless and have a plurality of modules. The wireless charging circuitry may be configured to transfer power from at least one, several or all of the of the modules or an attached (e.g., by USB) mobile computing device. Similar to synchronization button 230, the tie 2200 may also have an input configured to direct the plurality of electronic components to receive synchronization information from a wireless network. The tie 2200 may further contain an antenna. Wireless charging unit may be connected to wireless charging circuitry and may operate by magnetic resonance, inductive charging, or power over RF or similar wireless charging methods to provide power to or receive power from a nearby mobile computing device and/or modules (e.g., power modules) in the tie 2200. Along with the wireless charging unit there may be a battery located in the tie 2200 and in connection with the wireless charging unit and the wireless charging circuitry. The tie 2200 may include data ports providing outside connections to the tie 2200. The data ports may be microUSB, HDMI, NV inputs or the like and are linked wireless charging circuitry to the modules. One port may be a charging port to provide power to the wireless charging unit, a battery, the electronic components in the tie 2200 and/or an attached mobile computing device. The tie 2200 may include a wireless module which may be a WWAN modem to link the electronic device to 3G, 4G or other future network. Alternatively or additionally, another wireless module may be a WLAN modem to link the electronic device using WiFi, SuperWiFi, Bluetooth, WHDMI, or the like. Functionally these wireless modules will operate similarly to modules 214 and 216 as described above. A memory bank (similar to memory bank 218) may include a plurality of replaceable memory modules having internal storage such as SSD, flash memory, or the like. Since the memory bank (and its memory modules) may be in communication with the wireless modems, the tie is therefore configured to allow for simultaneous connection of the mobile communication device with the memory bank and through the wireless modem to a network. There may also be a module (similar to module 220) which may be sensory module and may contain a sensor chip which can detect biometric inputs such as finger prints, eye movement, face shape and the like.

Figure 23:
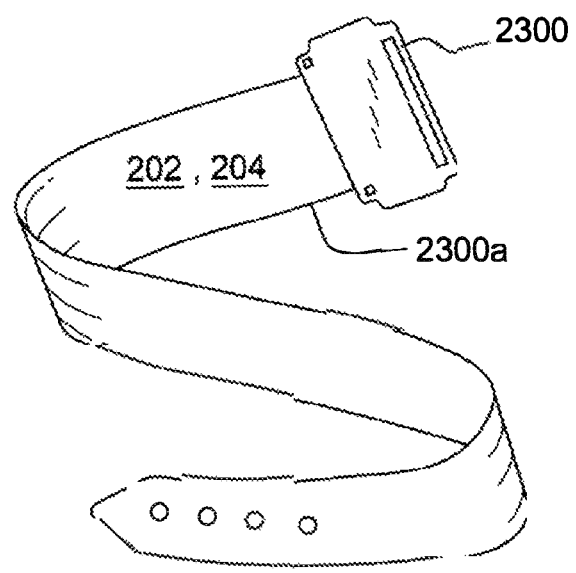
FIG. 23 illustrates an embodiment of the PCCC which has a belt shape.

FIG. 23 illustrates an embodiment 2300 of the PCCC which has a belt shape structure with a belt panel 2300a. As discussed with regard to previous embodiments above, belt 2300 provides a personal cloud to the user and access to wireless networks (such as 3G, 4G, WiFi, SuperWiFi, and similar wireless technologies). The structure 2300 may include the electronic components, modules (including WLAN and WWAN wireless modules), memory and power source as described above with regard to second panel 204 in FIG. 2A. However, it is also may include the wireless charging module 208 which is shown FIG. 2A mounted on the first panel 202. Electronics components in the belt 2300 such as controllers, memory modules, batteries, and the like may be entirely covered by the structural material. The structure 2300 may be made of clothe, leather and/or waterproof material. In alternative embodiments the structure 2300 may be made of any material (hard and/or soft) that makes the embodiment 2300 lightweight but durable and resilient such as plastic, silicone, ceramic, fabric, leather, steel, aluminum, fiberglass, titanium, Kevlar, and/or rubber. The belt 2300 may be rectangular in shape. Wireless charging circuitry may extend throughout the belt panel 2300a. The wireless charging circuitry can provide both power and serve as a data link. The wireless charging circuitry may be a flexible, ribbon cable. Wireless charging circuitry may be internal to the belt 2300 and extend along substantially the length of the belt panel 2300a. The wireless charging circuitry may be wireless and have a plurality of modules. The wireless charging circuitry may be configured to transfer power from at least one, several or all of the of the modules or to an attached (or detached) mobile computing device. Similar to synchronization button 230, the belt 2300 may also have an input configured to direct the plurality of electronic components to receive synchronization information from a wireless network. The belt 2300 may further contain an antenna. A wireless charging unit may be connected to the wireless charging circuitry and may operate by magnetic resonance, inductive charging, or power over RF or similar wireless charging methods to provide power to or receive power from a nearby mobile computing device and/or modules (e.g., power modules) on the belt 2300. Along with the wireless charging unit there may be a battery located in the belt 2300 and in connection with the wireless charging unit and the wireless charging circuitry. The belt 2300 may include data ports providing outside connections to the belt 2300. The data ports may be microUSB, HDMI, A/V inputs or the like and are linked wireless charging circuitry to the modules. One port may be a charging port to provide power to the wireless charging unit, a battery, the electronic components in the belt 2300 and/or an attached mobile computing device. The belt 2300 may include a wireless module which may be a WWAN modem to link the electronic device to 3G, 4G or other future network. Alternatively or additionally, another wireless module may be a WLAN modem to link the electronic device using WiFi, SuperWiFi, Bluetooth, WHDMI, or the like. Functionally these wireless modules will operate similarly to modules 214 and 216 as described above. A memory bank (similar to memory bank 218) may include a plurality of replaceable memory modules having internal storage such as SSD, flash memory, or the like. Since the memory bank (and its memory modules) may be communication with the wireless modems, the band is therefore configured to allow for simultaneous connection of the mobile communication device with the memory bank and through the wireless modem to a network. There may also be a module (similar to module 220) which may be sensory module and may contain a sensor chip which can detect biometric inputs such as finger prints, eye movement, face shape and the like.

Figure 24:
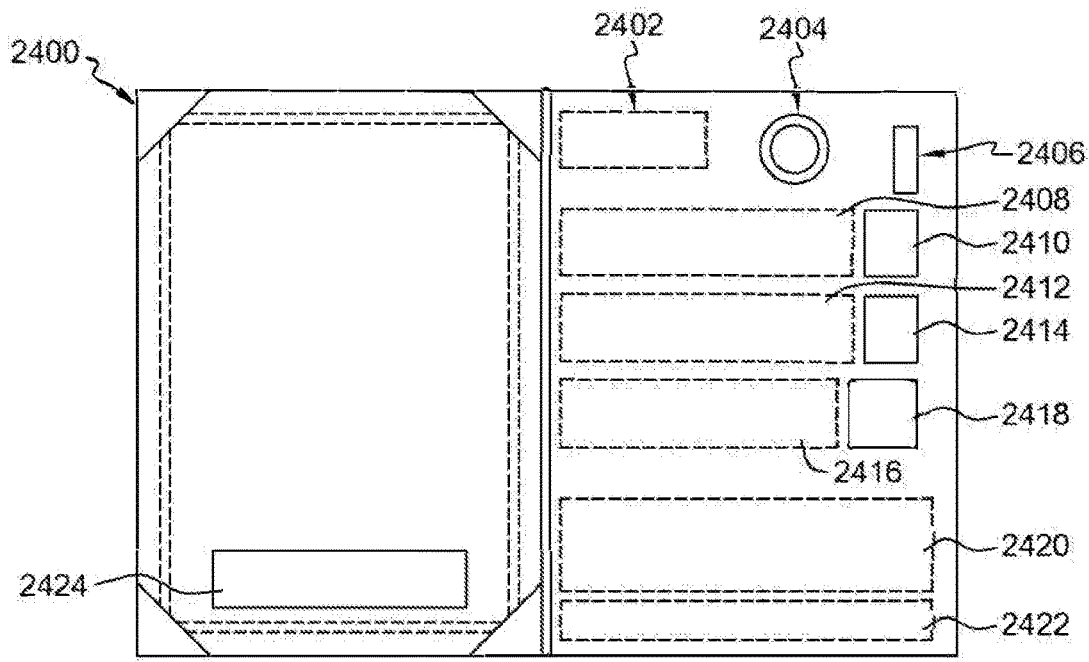
FIG. 24 illustrates an embodiment of the case cover having a medical health function.

FIG. 24 illustrates another embodiment of the PCCC which is a medical/health case cover 2400 made up of components to monitor human health. When it comes to monitoring human health, today's consumers are limited to so-called "health trackers" which count steps and calculate calorie burns. Traditional health trackers are only capable of measuring heart rate and are limited to external measurements. These devices are not capable of getting the internal body data; meaning they do not have access to human fluids. The personal cloud case cover gives users a health monitoring lab, with integrated biochips, microarray and other chip size medical analyzers. The health cover cannot only analyze human fluids but also fluids being consumed by the user (food and drinks). The data collected from the fluids is then compared to a cloud or local database. The results are displayed on a phone, tablet, PC, TV, or any other device connected to the health cover. Today people have to visit their doctors in order to perform fluid tests and get information about their health. The health cover can easily share the data with one's doctor over a secure network without a doctors visit. For example, doctors can ask their patients to submit blood samples through the personal health shield.

The medical/health case cover 2400 is a case with modular capabilities made of materials such as leather and/or plastic. It contains bio/mechanical/electrical components in one or two panels, meaning the case can have two panels/sides or only one side/panel. Modem 2402 may be WiFi, 3G, 4G, and 5G. To access highly secure health network that contains health database and access to thousands of medical professionals. Doctors can easily interact with the patient and compete for their business. Camera 2404 can analyze a human eye and share information with your doctor. Needles 2406 may be used to help draw blood. The needles are easily removable/swappable. Biochip module 2408 uses light to analyze liquids received through liquid input 2410. The liquids may be blood, drinks or any other type of liquid requiring analysis. Biochip module 2412 uses radio frequency (RF) to analyze inputs received through liquid input 2414. Microarray module 2416 analyzes inputs received through liquid input 2418. Internal database 2420 contains a database of the most common diseases and can be customized to a persons health. The database can be constantly updated. Also, shows the closest clinics and compares the costs and insurance coverage. Power source 2422 is used to power the case cover. Electrocardiogram (EKG) 2424 is capable of measuring problems with the electrical activity of the heart.

Figure 25:
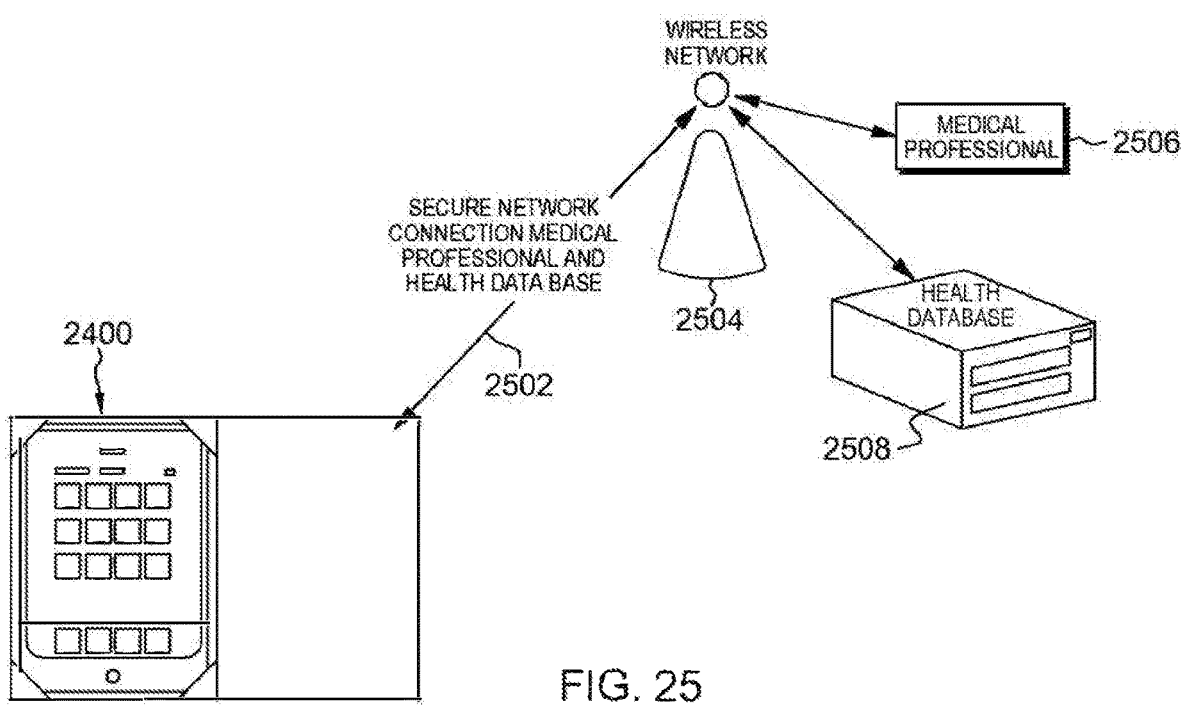
FIG. 25 illustrates the medical health case cover operating in a cloud environment.

FIG. 25 shows the medical/health case cover 2400 operating in a cloud (or network connection 2502 between the case cover 2400 and a cell tower 2504 to share data collected and/or analyzed at the case 2400 with a medical professional wireless device and/or health database 2508. In this example, the case cover is acting as a "hotspot" to provide network access for locally collected medical/health data. In another embodiment, link 2502 may be a wired connection.

Figure 26:
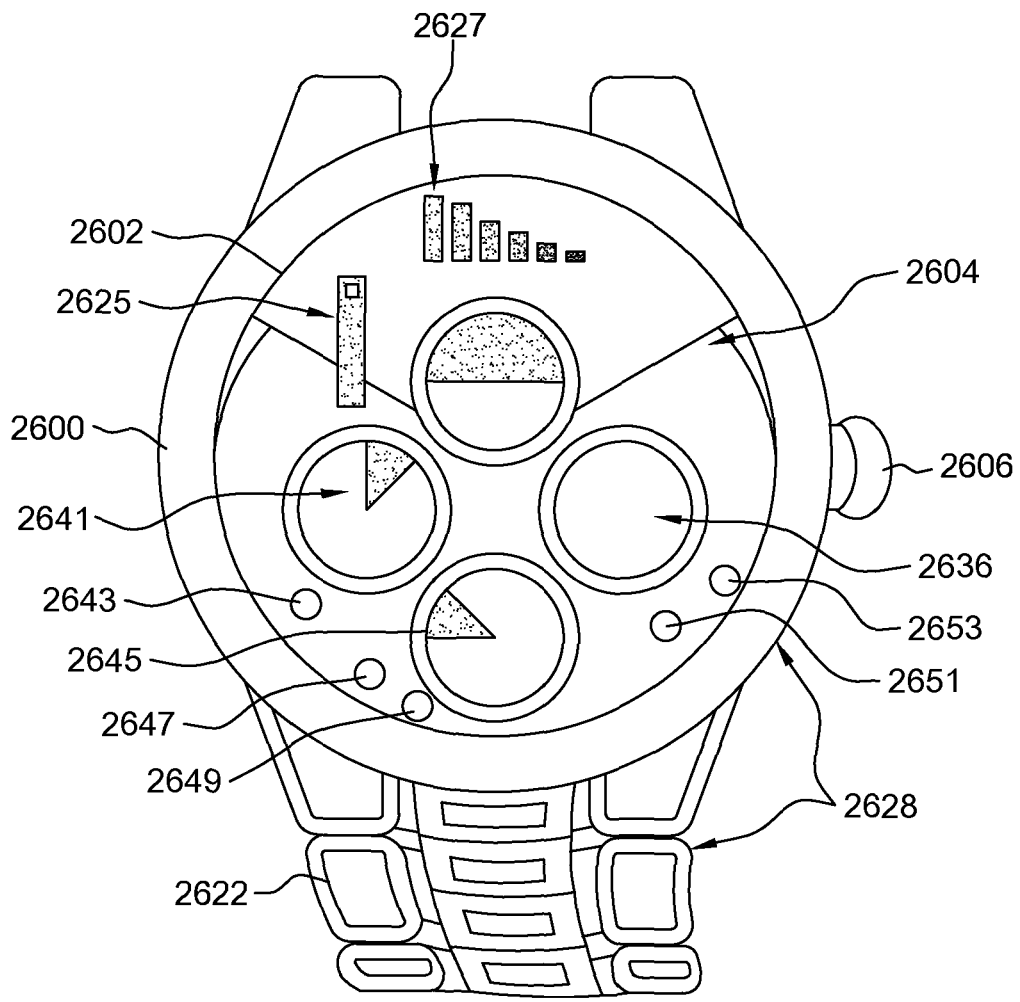
FIG. 26 is an environmental sensor having a plurality of environmental and physical detection functions.
Figure 27:
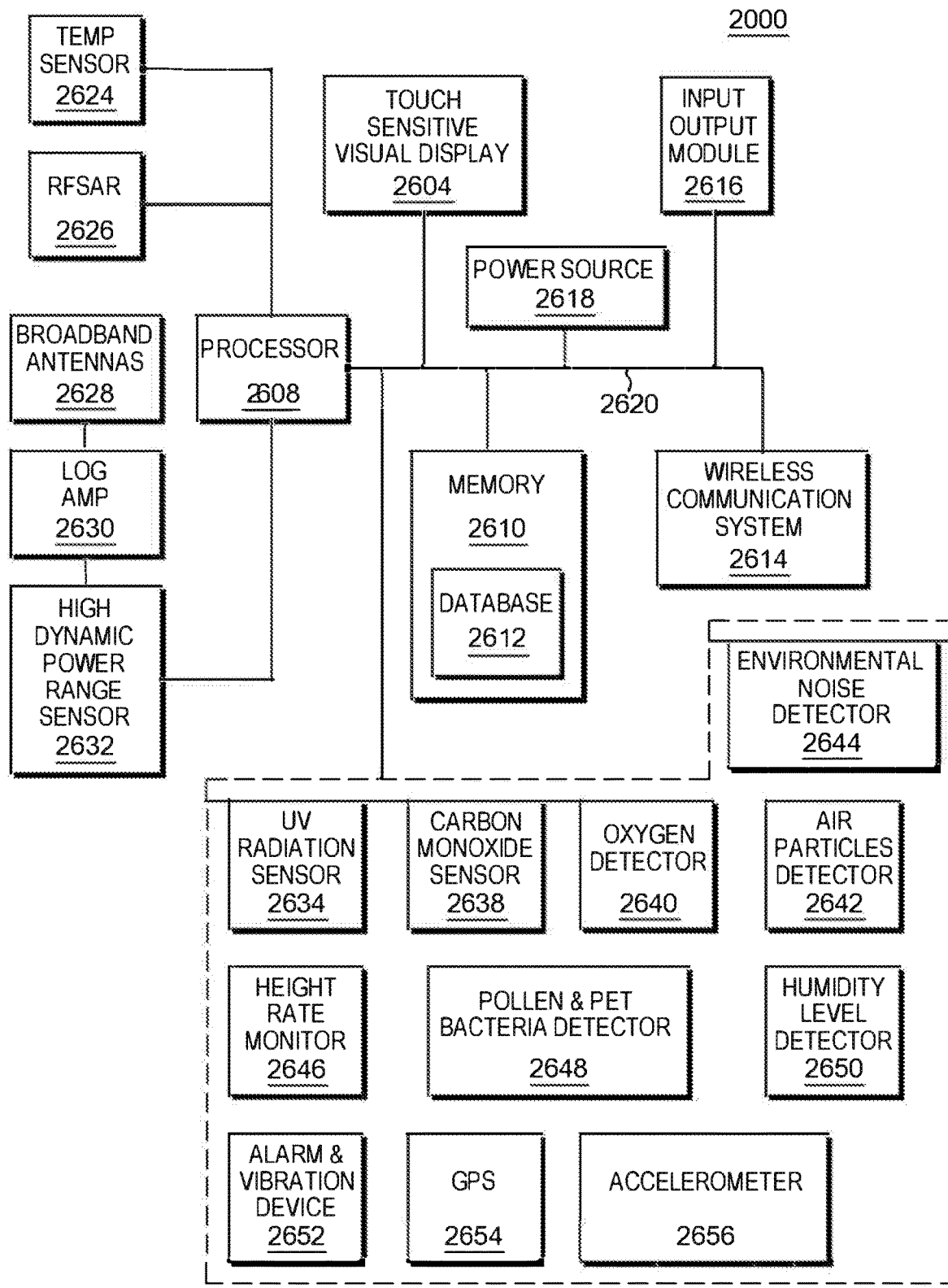
FIG. 27 is a block diagram of the circuitry of the environmental sensor.

FIG. 26 illustrates an environmental sensor (or wearable environmental sensor or universal sensor) embodiment 2600 capable of detecting environmental conditions and relaying the information to the user. FIG. 27 is a circuit diagram of the underlying electronic components of the environmental sensor 2600 contained in a housing 2602. The housing may be circular, square, or rectangular in shape or the like. The housing may broadly have a user interface system including a touch sensitive visual display screen 2604. In addition to inputting through the touch sensitive visual display 2604, the operator may input through buttons or actuators mounted on the sides of the housing surrounding the visual display (e.g., button 2606). The housing typically includes a processor 2608 which is communicatively coupled with the touch sensitive visual display screen 2604, a memory 2610 having a database 2612, a wireless communication system 2614, an input/output (I/O) module 2616 and a power source (e.g., battery) 2618. In a first time function, the processor 2608 will keep track of the time and display it in analog or digital form on the visual display screen 2604. The other functions of the environmental sensor 2600 may be performed over the background surface of the time or some other background selection stored in memory 2610. Exemplary housings 2602 may include a system bus 2620 and/or one or more interface circuits (not shown) for coupling the processor 2608 and other components (e.g., visual display 2604, memory 2610, wireless communication system 2614, I/O module 2616 and a plurality of sensors discussed below) to the system bus 2618 and to each other.

Typically, the processor 2608 is configured to execute instructions and to carry out operations associated with the environmental sensor 2600. For example, using instructions retrieved from the memory 2610 (e.g., a memory block), the processor 2608 may control the reception and manipulation of input and output data between components of the housing 2602. The processor 2608 is configured for capturing data from the plurality of sensors in the housing 2602, operate with an operating system to execute computer code to process the data and display the data on the visual display 2604. The operating system, other computer code, and data may reside within the memory 2610 that is operatively coupled to the processor 2608. The memory 2610 generally provides a place to store computer code and data that are used by the environmental sensor 2600. The memory 2610 may include Read-Only Memory (ROM), Random-Access Memory (RAM), and/or other non-transitory storage media. The operating system, other computer code, and data may also reside on a removable non-transitory storage medium that is loaded or installed onto the environmental sensor 2600 when needed. The wireless communication system 2614 may have a modem or a plurality of modems that enable the environmental sensor 2600 to communicate with a wireless network, such as a cellular network (e.g., a GSM network, a CDMA network, or an LTE network), a local area network (LAN), and/or an ad hoc network. The environmental sensor 2600 may further have a modem in the wireless communication system capable of communicating using Bluetooth™, WiFi, WiFi Direct or other wireless communication technology with a phone or hotspot and then to a phone base station. In some embodiments, the wireless communication system 2614 also allows the environmental sensor to communicate with a corresponding wireless communication system in another universal sensor. The wireless communication system 2614 may have a first low power transmitter or low power transmit mode which can last for extended time periods (e.g., several months) with little draw on the battery and without charging. In addition, the wireless communication system may and have a second high power transmitter or high power transmit mode which draws much more power from the battery and may typically be used in case of emergency when the base station is distant. The I/O module 2616 may be a hardwire connector which allows the environmental sensor 2600 to receive power and/or data when plugged in.

The environmental sensor 2600 may be worn on the body and its housing 2602 attached by a band 2622 to a body part such as wrist, leg, neck, or the like. The environmental sensor 2600 includes a plurality of different types of sensors to obtain a picture of either the surrounding conditions of the user or the condition of the user. The readings from the sensor may be in real-time or collected over a period of time. Reference item 2624 indicates a temperature sensor capable of measuring the ambient temperature around the environmental sensor 2600 and a corresponding temperature sensor display 2625 located on the visual display 2604. In addition to detecting the local temperature, temperature sensor 2624 can detect both the overall body temperature and a body part temperature if placed at different points on the body. For example, change in temperature in the wrists can signal medical problems such as hypothermia and running the environmental sensor housing containing the sensor 2624 across the forehead can detect core body temperature. The sensor 2624 can also detect the temperature of objects when placed on or in proximity to them (e.g., such as the temperature of a coffee mug). Reference item 2626 indicates a radio frequency specific absorption rate (RF SAR) sensor and indicator 2627 located on the visual display which measures the rate at which energy is absorbed by the human body. In addition, there could be a plurality of embedded antennas 2628 in the environmental sensor housing 2602 and the band 2622. Broadband antennas 2628 collect RF signals which are then forwarded to a logarithmic amplifier (i.e., log amp) 2630 which is connected to high dynamic power range sensor 2632. The data collected is analyzed in processor 2608 and shown on display 2627 on the screen of the environmental sensor. The environmental sensor 2600 includes a ultraviolet (UV) radiation sensor 2634 that detects the amount of UV absorption by the human body. UV is produced by the sun and can result in skin cancer. This sensor 2634 and UV rate indicator 2636 help users avoid UV radiation for a prolonged period of time. The environmental sensor 2600 includes a carbon monoxide sensor 2638 detects the presence of carbon monoxide (CO) gas in order to prevent carbon monoxide poisoning. Oxygen detector 2640 detects and displays the oxygen levels in the atmosphere around the environmental sensor 2600. Display 2641 shows the oxygen levels. Air particle detector 2642 is configured to detect hazardous air pollutants (HAP) that reduce air quality and the results are shown on indicator 2643 on the visual display. Light sensors in the environmental sensor could be used to predict HAPs. The light sensors could be connected to one or a plurality of ultrasound actuators that would clean the light sensors and allow restart of the collection process. Noise level detector 2644 has noise level speakers that track environmental noise. It is important to collect data on noise and display on an indicator 2645 so that the user can, for example, protect their hearing. The noise level detector 2644 may also be used for sleep tracking patterns to help insomnia patients understand their sleep patterns. Data can then be sent directly to the patient's doctor. Sensor 2646 is a heart rate monitor that checks the heartbeat of the wearer and displays on indicator 2647 the current heart rate in beats per minute and/or puts out a signal that an irregular heartbeat is occurring. Sensor 2648 detects pollen and pet bacteria by periodically sampling the air surrounding the environmental sensor and displaying on indicator 2649. Humidity levels in the surrounding air may be detected by sensor 2650 and shown on indicator 2651. The environmental sensor 2600 has an alarm and vibration device 2652 and indicator 2653 that allows for both type of annunciators to be set and heard and/or felt by the operator. The environmental sensor 2600 may have an internal GPS 2654 or rely on base station towers to provide the location of the environmental sensor 2600. In addition, the environmental sensor may have an accelerometer 2656 that may be used to (along with the GPS 2654) detect the height of the environmental sensor 2600 from the ground. Sensors 2634, 2638, 2640, 2642, 2644, 2646, 2648, 2650, 2652, 2654, and 2656 are connected through bus 2620 to processor 2608 for purposes of analysis. The collection of data from a plurality of environmental sensors 2600 further allows for analysis of environmental conditions on a global scale in approximately real-time. Temperature change could be detected with much finer detail across large areas. The environmental sensor 2600 may have all or a combination of a plurality of the sensors listed in the discussion above.

Figure 28:
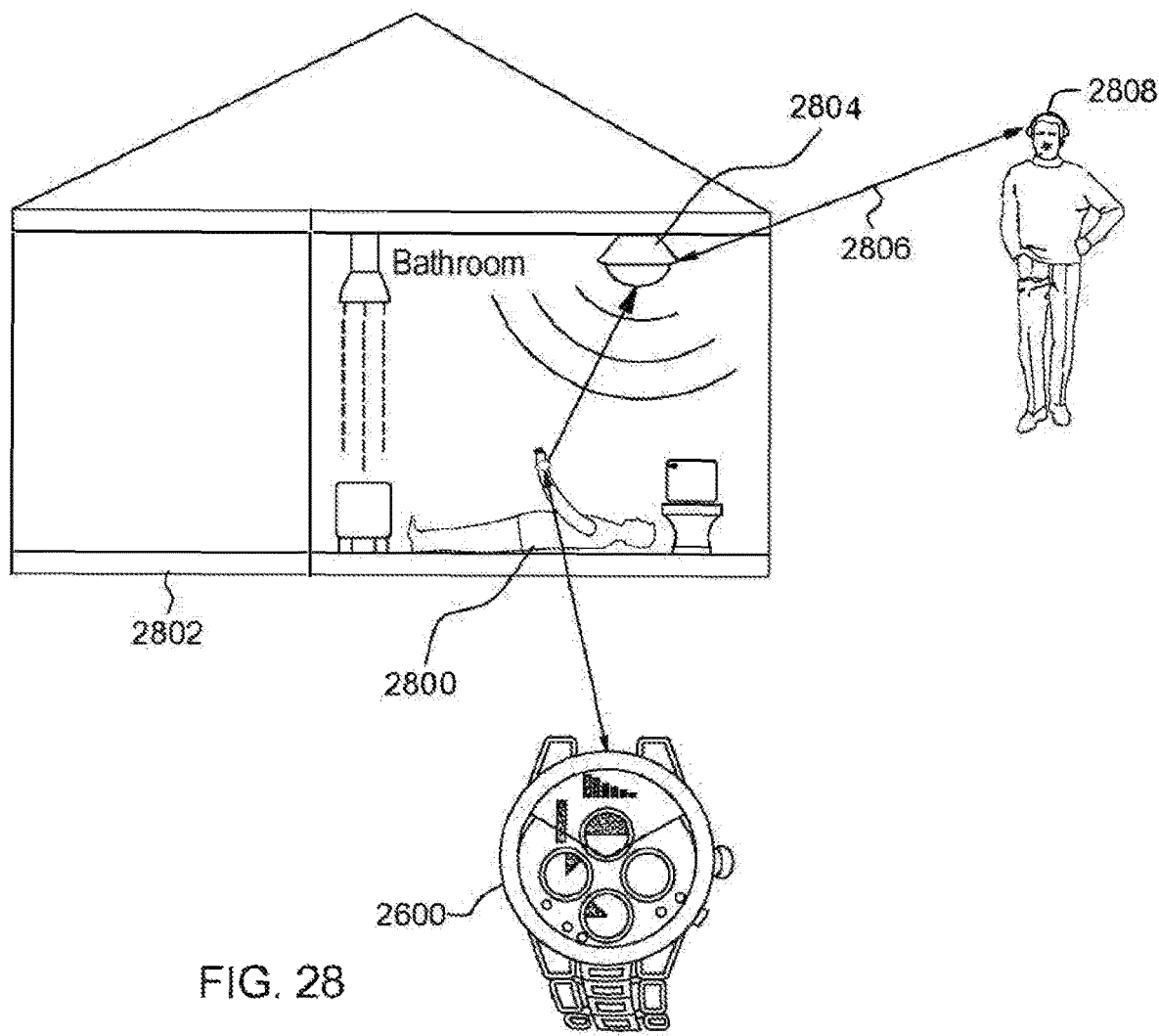
FIG. 28 is a schematic of the environmental sensor operating in a networked environment.
Figure 29:
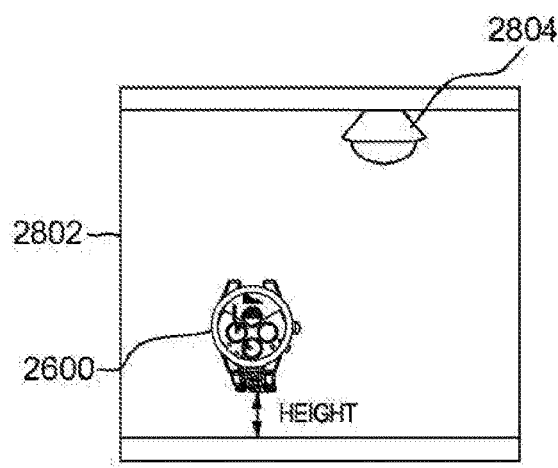
FIG. 29 is a close up schematic of the environmental sensor indicating a fall determined by its height and location.

FIG. 28 shows the environmental sensor 2600 in an operational environment. In this embodiment, environmental sensor 2600 monitors vital signs (such as heart rate using sensor 2646) of a person 2800. In memory 2610, the environmental sensor may have stored the medical history of the person 2800. The medical history could be encoded into identifications in the environmental sensor 2600. FIG. 28 shows the person 2800 wearing the environmental sensor 2600 has fallen in the bathroom of a dwelling 2802. Handy Base Station 2804 is located in the bathroom. The Handy Base Station (HBS) is described in detail in U.S. patent application Ser. No. 14/658,183, filed on Mar. 14, 2015, entitled "Handy Base Station System, Device and Method" which is owned by the Assignee of this Application and is hereby incorporated by reference. The HBS may be a lamp housing that in addition to providing light through LEDs may contain a processor and a plurality of wireless communication modems to link the HBS with a base station and a network (e.g., Internet). The HBS may have any combination (or all) of a plurality of modems such as WWAN, WLAN, WiFi, WiFi Direct and Bluetooth. HBS 2804 receives a wireless communication from the environmental sensor 2600 which obtained a reading from its accelerometer 2656 that based on the height and location (see FIG. 29) of the environmental sensor 2600 or the rapid height change, the person 2800 has taken a fall. HBS 2804 is programmed to send a message to the environmental sensor 2600 for display on the visual display screen 2604 asking the person if they are okay or if they need an ambulance. In an alternative embodiment, the HBS 2804 may have a speaker to request a response from the person 2800 and act based on if a response is received. If the person does not respond to either a message or a voice communication from the HBS 2804 within a predetermined time (e.g., 1-2 minutes), the HBS will send a 911 request over wireless link 2806 to a 911 operator center 2806 for an ambulance. In another embodiment, if a fall occurs, the environmental sensor 2600 itself could also automatically send out a 911 request using its wireless communication system 2614. In this instance, the wireless communication system could go into high power mode to send a signal to a base station and also send the medical history and vital signs of the person 2800.

As the new wireless mobile and fixed standards keep pushing the operating frequencies into the millimeter wave (mmWave) spectrum (i.e., about 17 GHz to 300 GHz such as, for example, about 24 GHz, 28 GHz, 40 GHz, 60 GHz, 70 GHz, and/or 100 GHz) and in the range of about 10 GHz to 300 GHz it becomes harder and harder to transmit signals inside buildings, houses, cars and other objects or obstacles. Even mobile phone casings may prevent mmWave signals to get in or out of the mobile phone. These challenges limit the usability of mmWaves and make them very expensive to use. The disclosed embodiments make mmWave signal penetration possible.

Figure 30:
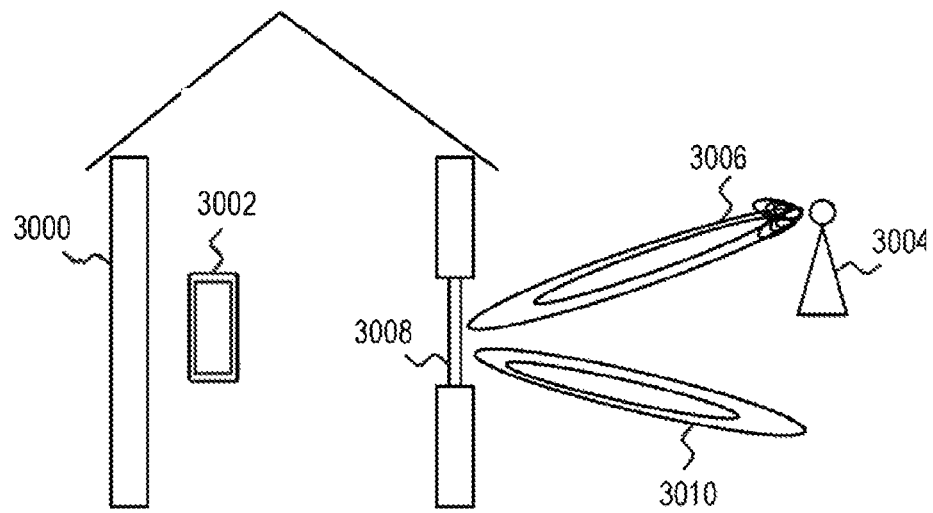

FIG. 30 illustrates such a problem of wireless signals trying to enter building 3000 to access device 3002 which could be a wireless device such as a mobile phone, Internet of Things (IoTs) device, and the like or a wired device such as a cable box. For purposes of this description, device 3002 will be a wireless device such as an iPad. The base station 3004 (e.g., small cell, distributed antenna system, Pico cell, and/or Femto cell) transmits signals 3006 to wireless device 3002 but all or a significant portion of the signals will be reflected off a barrier (e.g., window) 3008 and scattered 3010.

Figure 31:
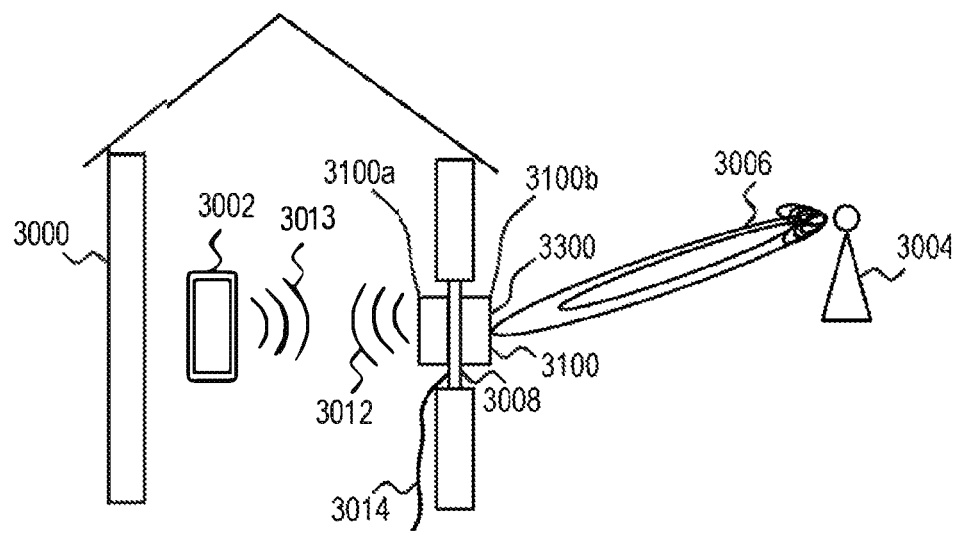
FIG. 31 shows the signal 3006 being transmitted from the cell tower 3004 to a cordless mm Wave antenna device 3100 connected to a corresponding internal device 3102.
Figure 39:
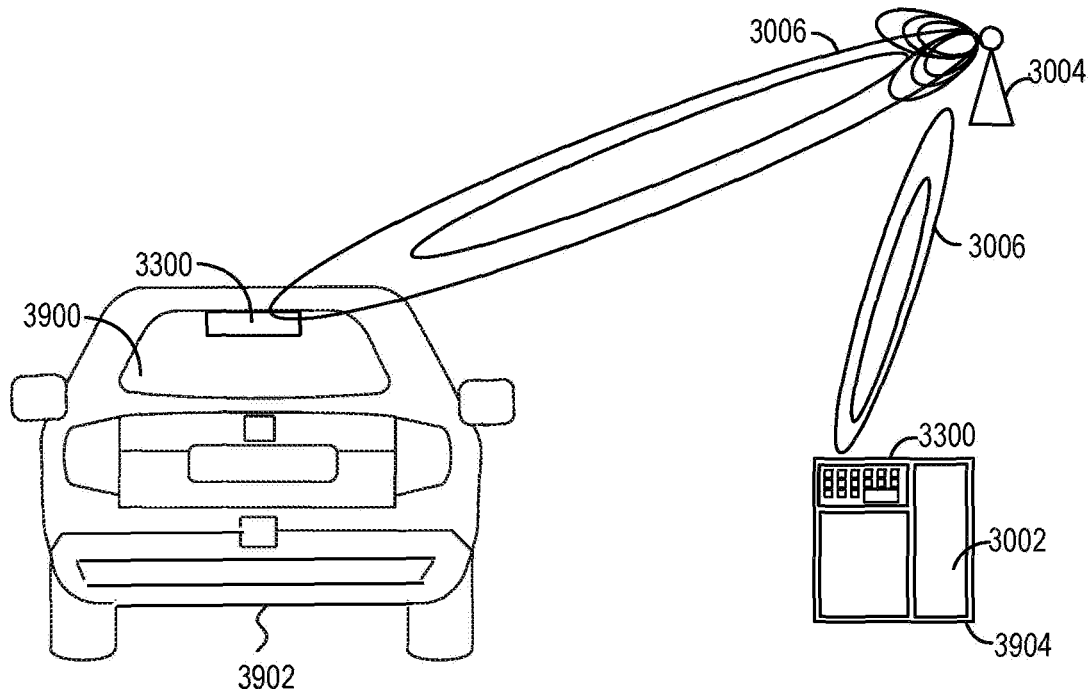
FIG. 39 shows a low cost antenna array/panel made/printed on a thin film material built into a car window.

FIG. 31 shows the signals 3006 being transmitted from the base station 3004 to a communication device (or system) 3100 able to receive signals 3006 and connect them wirelessly 3012 to at least one wireless device 3002 of a possible plurality of devices located inside the building 3000. Signals 3006 may be in the millimeter wave (mmWave) spectrum (i.e., about 17 GHz to 300 GHz such as, for example, about 24 GHz, 28 GHz, 40 GHz, 60 GHz, 70 GHz, and/or 100 GHz) or in a range of 10 GHz to 300 GHz (e.g., about 10 GHz to 100 GHz, about 30 GHz to 300 GHz). The device 3100 is also capable of receiving signals 3013 from the wireless device 3002 and transmitting them to the base station 3004. The device 3100 is a two part device made up of an internal (e.g., indoor) unit 3100a and an external (e.g., outdoor) unit 3100b. The two units of the device 3100 may be connected to both sides of a barrier or obstacle such as a window 3008 of building 3000 or a wall of building 3000. In alternative embodiments, instead of a building, the device 3100 may be mounted on and inside a vehicle 3902 as shown in FIG. 39 (discussed below). The barrier 3008 may be a glass window, a vehicle panel, a frame or some type of section made of a dielectric material. When installed, the two units 3100a, 3100b are typically located in "proximity" to each other (i.e., about ⅛ inch to 3 feet). The device 3100 can be used any there is a barrier that prevents mmWave transmission. The device 3100 can be easily attached to any surfaces using magnets, suction cups, or other form of attachment mechanism. The device 3100 can be located inside and outside houses, buildings, and/or cars. The device 3100 may use an antenna array 3300 which is discussed in detail below in relation to FIG. 33.

Figure 32:
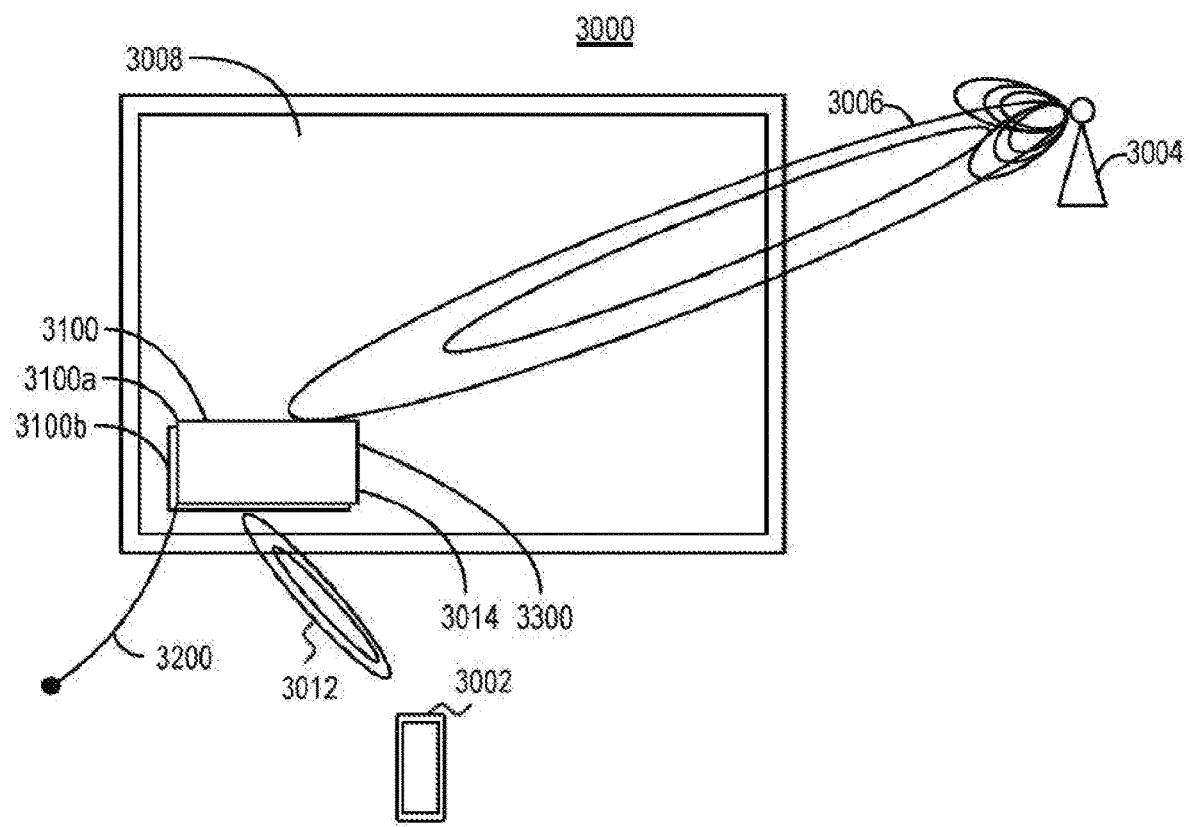
FIG. 32 shows a view from inside a building looking through window 3008 to the cell tower 3005.

FIG. 32 shows a view from inside the building 3000 looking through window 3008 to the base station 3004. Device 3100 is shown attached to both sides of window 3008. The outdoor unit 3100b receives signals 3006 from base station 3004, down converts the signals to a lower frequency (e.g., less than about 9 GHz), and wirelessly relays the signals to indoor unit 3100b on the other side of the window 3008. The protocol for the signals 3012 sent from indoor unit 3100b to wireless device 3002 may be WiFi, Zigbee, Bluetooth, Long Term Evolution (LTE), LTE-Advanced (LTE-A), LTE-Unlicensed Spectrum (LTE-U), and/or LTE License Assisted Access (LTE-LAA), 4G, and/or 5G. Alternatively, the indoor unit 3100a may be hardwired to a cable 3014 (e.g., Ethernet cable) and transmit the signal in that manner to routers and other devices. This system and method allows RF signals to easily penetrate the inside of the building 3000 as well as allow for signals from device 3002 to be converted to mmWaves or in the range of about 10 GHz to 300 GHz and transmitted to base station 3004.

Indoor unit 3100a may be powered from electrical receptacle 3200 as shown in FIG. 32. However another challenge is getting power to the outdoor unit 3100b on the outside as most buildings 3000 do not have wall outlets outside. As discussed below in detail, indoor unit 3100a is capable of wirelessly transmitting power to the outdoor unit 3100b from wall outlet 3100. Not only does device 3100 allow for RF signals to pass-through from outside to inside, but also allows power to be supplied through the window 3008 (or wall) of building 3000 from wall outlet 3200. The through window or through wall power supply transmission may be accomplished by two coils. A first coil 3366 located inside the building and a second coil 3365 located on the outside of the building (which will be discussed in detail below).

Figure 33:
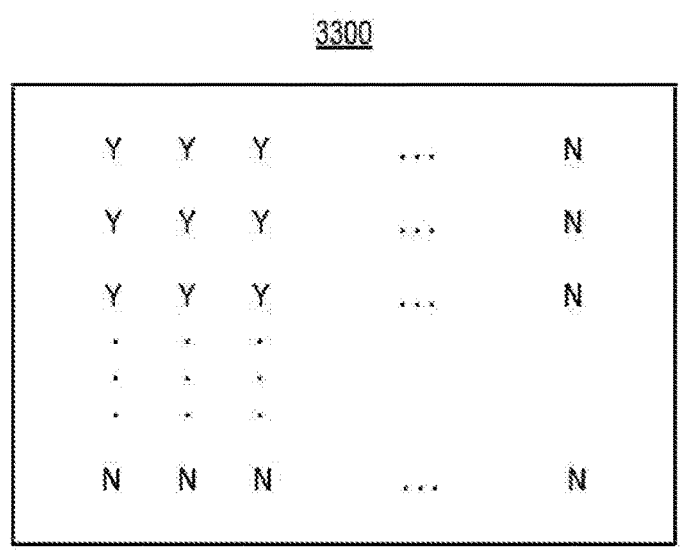
FIG. 33 shows a front view close up of antenna array 3300.

FIG. 33 shows a front view close up of antenna array 3300. Antenna array 3300 is a low cost antenna array in the form of a panel made and/or printed on a thin film material. It can be easily attached to any surfaces (e.g., glass) without obstructing views or the look of the surfaces that it is being attached to. The antenna array 3300 can be applied and/or attached to windows 3008, walls, smartphones, mobile phone casings, PCCCs and the like. The antenna array 3300 is made up of a plurality of N antennas arranged in a matrix. The matrix of antennas may be 4×4, 8×8, 12×12, and greater. The antenna array 3300 can capture mmWave signals (i.e., about 30 GHz to 300 GHz such as, for example, approximately 24 GHz, 28 GHz, 39 GHz, 40 GHz, 60 GHz, 70 GHz, 77 GHz and/or 100 GHz). The antenna array 3300 can also capture GPS signals and cellular signals (e.g., about 3.5 GHz or 5 GHz). The antenna array 3300 can be located inside or outside buildings 3000 and/or cars. Radio wave beams can be formed and steered by adjusting the phases of signals transmitted or received from the elements of the antenna array 3300. Antennas 3302, 3330, 3338, and 3358 discussed below may all be antenna arrays as described herein.

Figure 34:
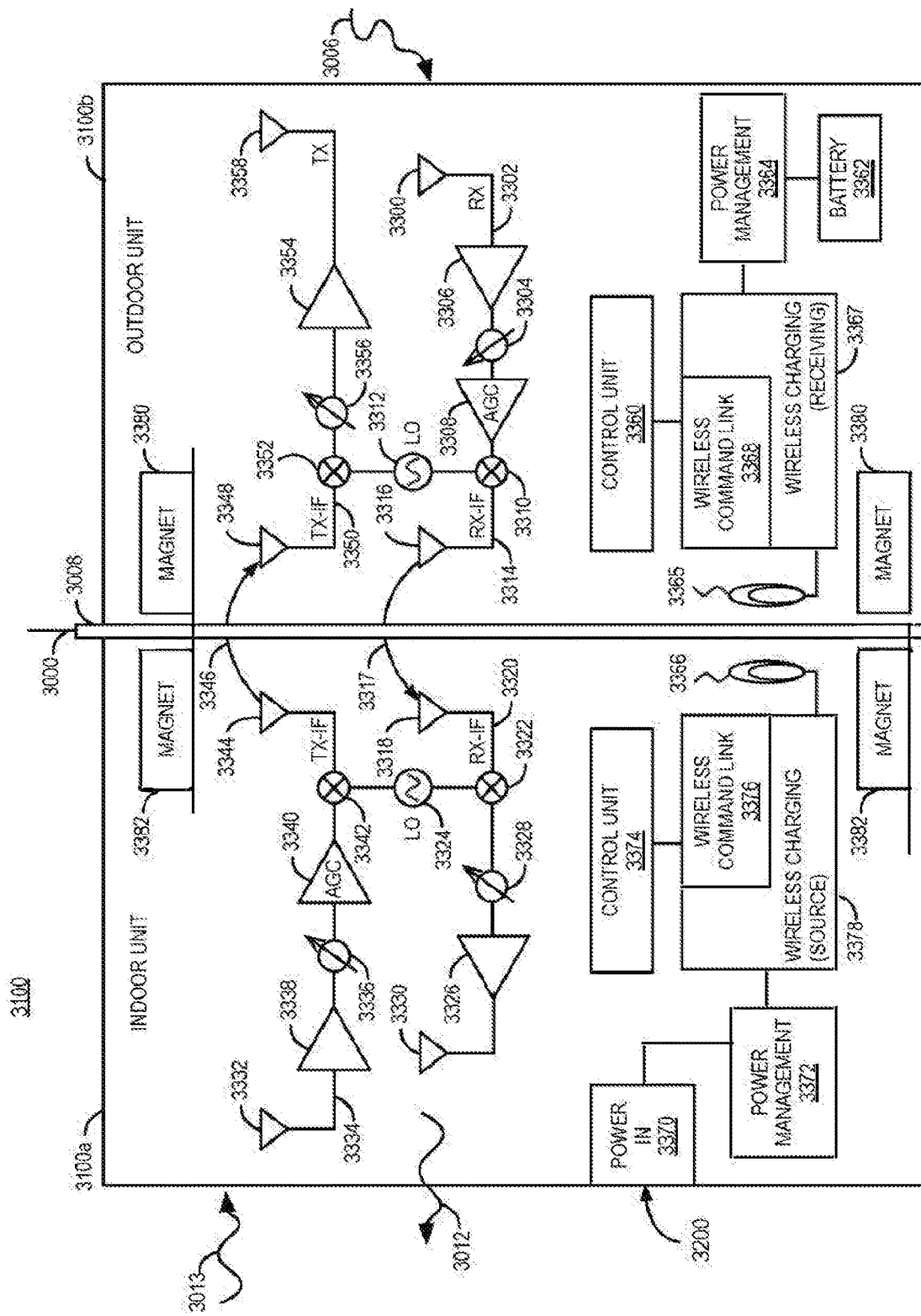
FIG. 34 shows a schematic of a repeater application of device 3100 attached to window 3008.

FIG. 34 shows a schematic of a repeater application of device 3100 attached to window 3008. The signal 3006 from base station 3004 enters outdoor unit 3100b of device 3100 at receiver antenna array 3300. The antenna array 3300 can capture millimeter wave (mmwave) signals (i.e., about 17 GHz to 300 GHz such as, for example, about 24 GHz, 28 GHz, 40 GHz, 60 GHz, 70 GHz, and/or 100 GHz) and signals in the range of about 10 GHz to 300 GHz (e.g., about 10 GHz to 100 GHz). The antenna array 3300 can also capture global positioning system (GPS) signals and microwave signals (e.g., about 1 GHz to 30 GHz). The signal travels on transmission line 3302, is amplified by low noise amplifier 3306, travels through phase shifter 3304 and enters automatic gain control circuit 3308 to ensure that the received signal is consistently amplified to a level that allows for efficient processing by the demodulation circuitry. The RF signal is input to the mixer 3310 controlled by local oscillator 3312 to down convert the frequency of the mmWave RF signal (or signal in the range of about 10 GHz to 300 GHz) to an intermediate microwave frequency signal (e.g., about 1 GHz to 9 GHz). The signal is then transmitted through line 3314 to antenna 3316 and now is at a frequency that a wireless signal 3317 can now easily wirelessly penetrate glass 3008 to be received at proximate antenna 3318 of indoor unit 3100a.

From antenna 3318 the signal travels through transmission line 3320 to mixer 3322 controlled by local oscillator 3324. Here the signal, for example, may be upconverted to a mmWave signal (or signal in the range of about 10 GHz to 300 GHz) for transmission within the building. The signal is then forwarded through phase shifter 3328 to power amplifier 3326 and then to antenna 3330. Antenna 3330 wirelessly transmits the signal 3012 to any wireless device such as 3002 located inside building 3000 in a plurality of different wireless protocols as discussed above. These protocols may include WiFi, Zigbee, Bluetooth, Long Term Evolution (LTE), LTE-Advanced (LTE-A), LTE-Unlicensed Spectrum (LTE-U), and/or LTE License Assisted Access (LTE-LAA), 4G, and/or 5G. In addition, the signal 3012 may be a mmWave signal in the range of about 17 GHz to 300 GHz (such as, for example, about 24 GHz, 28 GHz, 40 GHz, 60 GHz, 70 GHz, and/or 100 GHz) or a signal in the range of about 10 GHz to 300 GHz). Typically, signals internal to a building are WiFi signals and any addition to this WiFi protocol signals will lead to interference. However, when signal 3012 is a mmWave signal or a signal in the range of about 10 GHz to 300 GHz, it can re-transmit within the building basically the same, original signal that was received at antenna array 3300.

Correspondingly, mobile device(s) 3002 can transmit signals 3013 to antenna 3332. Antenna 3332 may be an antenna array. These signals may also be mmWave signals in the range of about 17 GHz to 300 GHz (such as, for example, about 24 GHz, 28 GHz, 40 GHz, 60 GHz, 70 GHz, and/or 100 GHz) or a signal in the range of about 10 GHz to 300 GHz (e.g., about 10 GHz to 100 GHz). The signals travels through line 3334, amplifier 3338, phase shifter 3336, automatic gain controller 3340, and mixer 3342 also controlled by local oscillator 3324 to antenna 3344. Wireless signal 3346 is transmitted from antenna 3344 through glass 3008 to antenna 3348. The signal travels through line 3350, mixer 3352 controlled by local oscillator 3312, phase shifter 3356 and amplifier 3354 to antenna 3358. (In an alternative embodiments, a switch could be added to outdoor unit 3100b and instead of antenna 3358, the signal could be transmitted by antenna array 3300). Note that phase shifters 3304, 3328 3336, and 3356 can be advantageously placed in the signal transmission or receiving path for beam forming and steering purposes (or capabilities).

Control unit 3360 controls operation of outside unit 3100b. Battery 3362 provides power for operation of outside unit 3100b. The charge and discharge functions of battery 3362 are controlled by power management unit 3364. Coil 3365 receives power from coil 3366 of the indoor unit 3100a. Coil 3365 is transfers power to wireless charging unit 3367. Wireless command link 3368 receives information through coil 3365 from the power signal from coil 3366 and allows for control unit 3360 to receive operating instructions wirelessly.

Electrical receptacle 3200 is coupled to input 3370 of indoor unit 3100a. Power is provided to power management unit 3372 which is controlled by control unit 3374. Indoor and outdoor control units 3374 and 3360 communicate with each other by wireless command links 3376 and 3368 through coils 3366 and 3365. Wireless charging source 3378 is connected to coil 3366 to wirelessly provide power to coil 3365 of the outside unit 3100b. The power may be transferred from the indoor unit 3366 to outdoor coil 3365 by electromagnetic coupling or resonance.

Magnets 3380 provide a secure attachment through glass 3008 to corresponding magnets 3382 mounted inside the building 3000.

Figure 35:
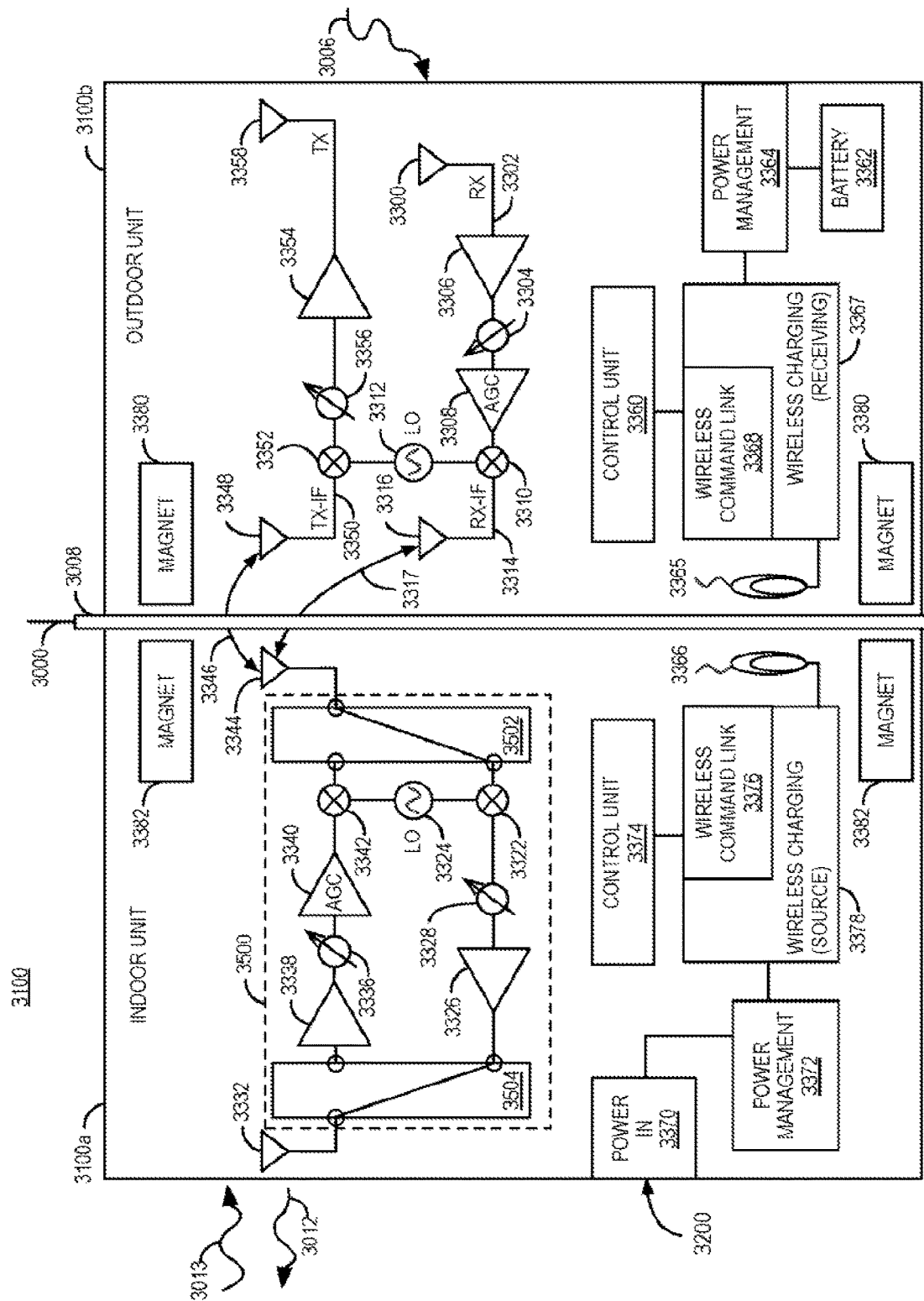
FIG. 35 shows a schematic of another embodiment of the repeater application of device 3100 with a switched transceiver 3500.

FIG. 35 shows a schematic of another embodiment of the repeater application of device 3100 with a switched transceiver 3500. Switched transceiver operates in a manner similar to FIG. 34 except that switches 3502 and 3504 have been added to eliminate the need for antennas 3330 and 3318. In this embodiment, wireless signal 3317 passes between antenna 3316 and 3344. Also, antenna 3332 receives signal 3013 and transmits signal 3012.

Figure 36:
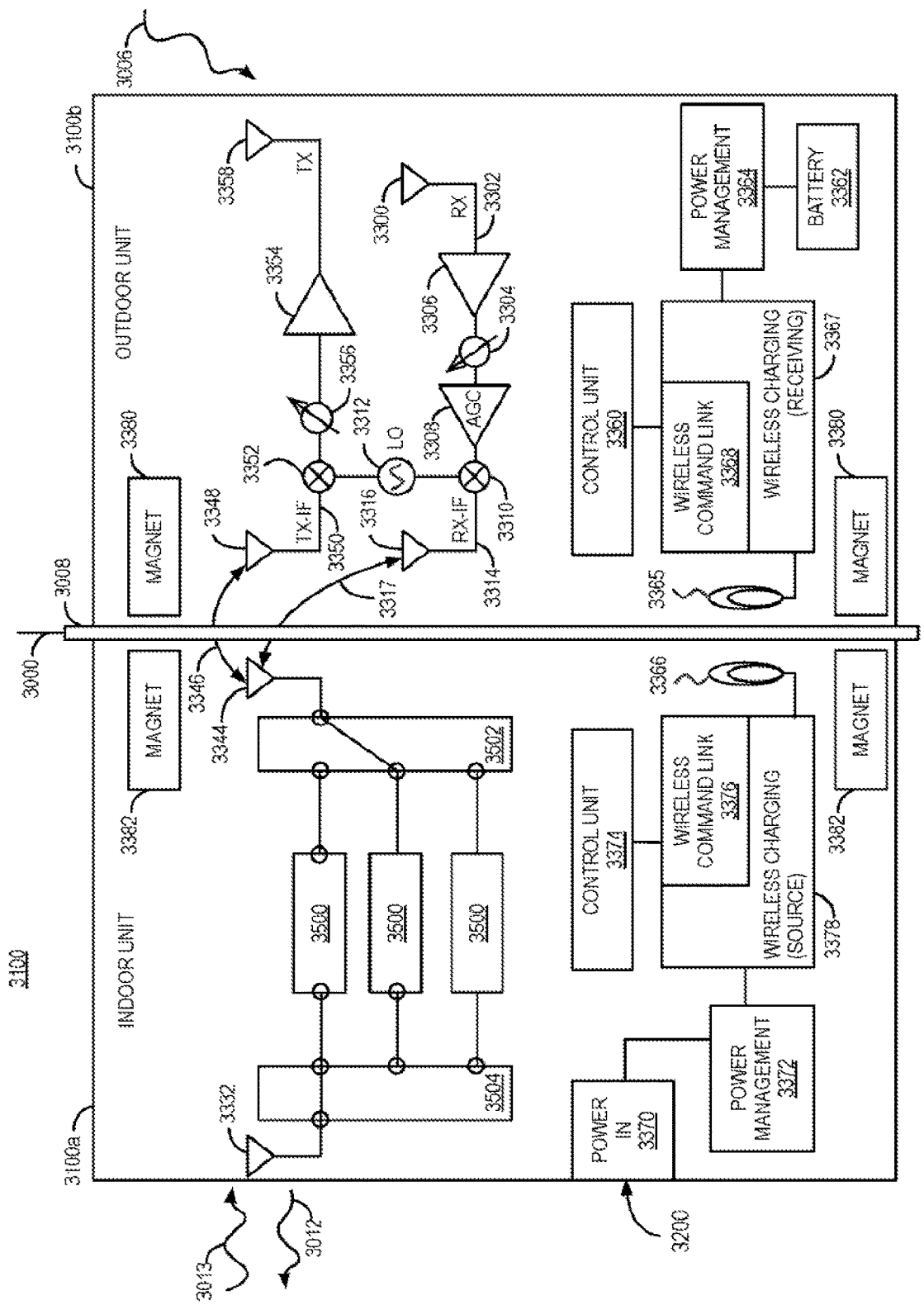
FIG. 36 shows a schematic of another embodiment of the repeater application of device 3100 with a plurality of switched transceivers 3500.

FIG. 36 shows a schematic of another embodiment of the repeater application of device 3100 with a plurality of switched transceivers 3500. In this embodiment, a plurality of transceivers 3500 are addressed using switches 3502 and 3504. The transceivers can transmit in a variety of protocols such as discussed above (e.g., WiFi, Zigbee, Bluetooth, Long Term Evolution (LTE), LTE-Advanced (LTE-A), LTE-Unlicensed Spectrum (LTE-U), and/or LTE License Assisted Access (LTE-LAA), 4G, and/or 5G).

Figure 37:
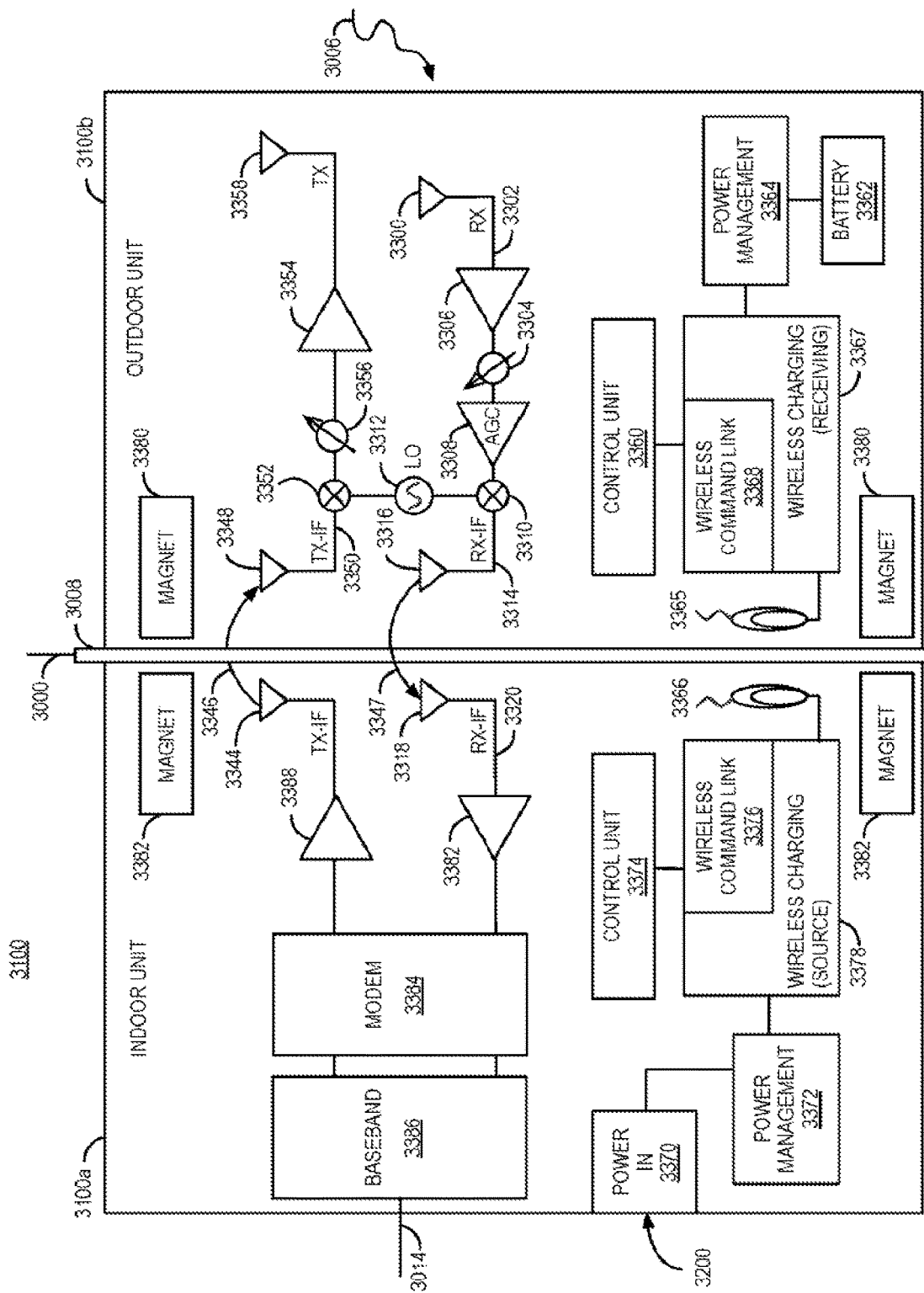
FIG. 37 shows a schematic of a small cell application of device 3100.

FIG. 37 is a small cell application of the device 3100. Many of the same elements are present in FIG. 34 as in FIG. 33 except for the following changes. Signal is received at antenna 3318 and transferred to amplifier and then to modem 3384 for demodulation. Baseband processor 3386 modulates digital signal to analog signal for transmission and also demodulates received analog signal to digital signal. An outbound signal is amplified by amplifier 3388 and transmitted through antenna 3344. An inbound signal is received by antenna 3318 and amplified by amplifier 3382. The signal is then passed to cable 3014 (e.g., Ethernet cable) and to devices such as TVs and the like.

Figure 38:
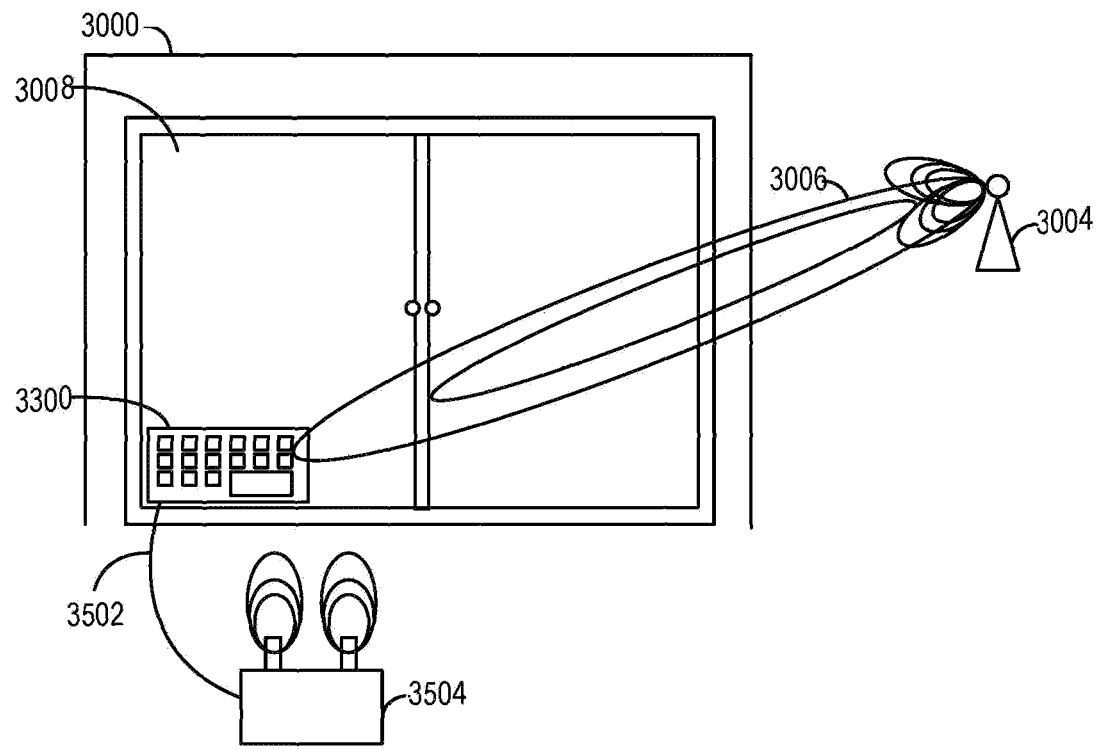
FIG. 38 shows an antenna array 3300 attached to a window 3008.

FIG. 38 shows an alternate embodiment with antenna array 3300 attached to window 3008 to address the limitations on use of mmWaves or signals in the range of about 10 GHz to 300 GHz (e.g., about 10 GHz to 100 GHz). The typical horn antenna (i.e., an antenna that consists of a flaring metal waveguide shaped like a horn to direct radio waves in a beam) for mmWaves is expensive, hard to install and heavy. The disclosed embodiments make the mmWave signal penetration possible. Since the low cost antenna array 3300 can be printed on a thin film material, installation is very easy as the antenna array 3300 is light and can attach to any object. The antenna array 3300 can also be any shape or size to blend in with the environment. In FIG. 38, the antenna array sits outside on a ledge of a window 3008 and is hardwired through a cable 3502 to user equipment 3504. Signals 3006 received at antenna array 3300 are down converted to lower frequency (e.g., about 1 GHz to 9 GHz) signals and sent through a cable 3502 to user equipment 3504. User equipment 3504 may be a wireless transmitting device which sends wireless signals in a wireless protocol standard discussed below to phones, tablets, TVs, and other devices located inside building 3000. Cable 3502 carries the RF signals received and sent to and from the antenna array 3300. Cable 3502 also provides control signals and power supply for the antenna array 3300 from the user equipment 3504. The cable 3502 can carry radio frequency signals from in a range from approximately 1 MHz up to 9 GHz. The cable can be short (less than 3 feet) or long (3 feet or greater). The user equipment 3504 contains the processing power (CPU, baseband, modem, and the like) to handle the received and sent signals 3006 to and from the antenna array 3300 from base station 3004. The user equipment also contains communication modules for transmitting in different wireless standards such as WiFi, Zigbee, Bluetooth, Long Term Evolution (LTE), LTE-Advanced (LTE-A), LTE-Unlicensed Spectrum (LTE-U), and/or LTE License Assisted Access (LTE-LAA), 4G, and/or 5G. The user equipment 3504 can act as a small cell or WiFi access point (AP). The user equipment 3504 may contact the user to the outside base station 3004 through the antenna array 3300.

FIG. 39 shows a low cost antenna array 3300 which may be printed on a thin film material built either onto or embedded within a barrier (e.g., a window, panel of a vehicle 3902, some type of dielectric material) 3900 of the vehicle 3902. The antenna array 3300 can be baked into any vehicle window 3900 at low cost. The antenna array 3300 makes beam forming and steering possible from the base station 3004. A traditional approach such as a horn antenna would not have such features.

FIG. 39 also shows a low cost antenna array 3300 made into a panel or printed on a thin film material built into a mobile phone case 3904 (or a PCCC 200) for wireless device 3002. Alternatively, the antenna array 3300 may be attached to the back of the wireless device 3002. Alternatively, the antenna array 3300 may be printed on or attached to a glass cover surrounding the phone case 3904 or PCCC 200. As discussed, antenna array 3300 makes beam forming and steering possible.

Figure 40:
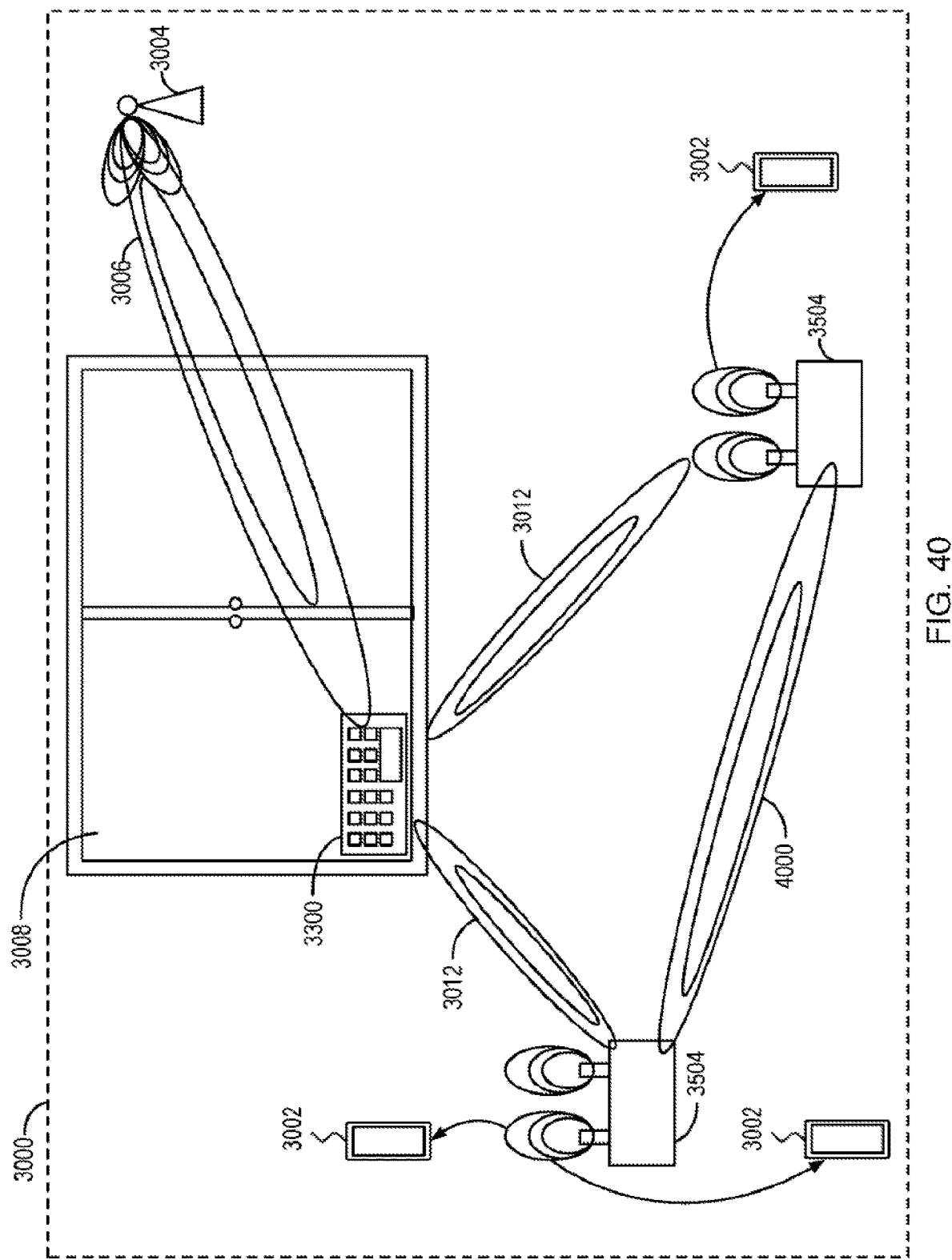
FIG. 40 illustrates an antenna array 3300 built into, located on, or printed into glass window 3008 of a building 3000.

FIG. 40 illustrates an antenna array 3300 built into, located on, or printed into glass window 3008 of a building 3000 to receive mmWave signals from base station 3004. Antenna array 3300 is wirelessly connected through signals 3012 to user equipment devices 3504 which are capable of a communicating with a plurality of wireless devices 3002 and with each other through wireless signal 4000. User equipment devices 3504 can relay signals from antenna array 3300 in different wireless standards such as WiFi, Zigbee, Bluetooth, Long Term Evolution (LTE), LTE-Advanced (LTE-A), LTE-Unlicensed Spectrum (LTE-U), and/or LTE License Assisted Access (LTE-LAA), 4G, and/or 5G.

Figure 41:
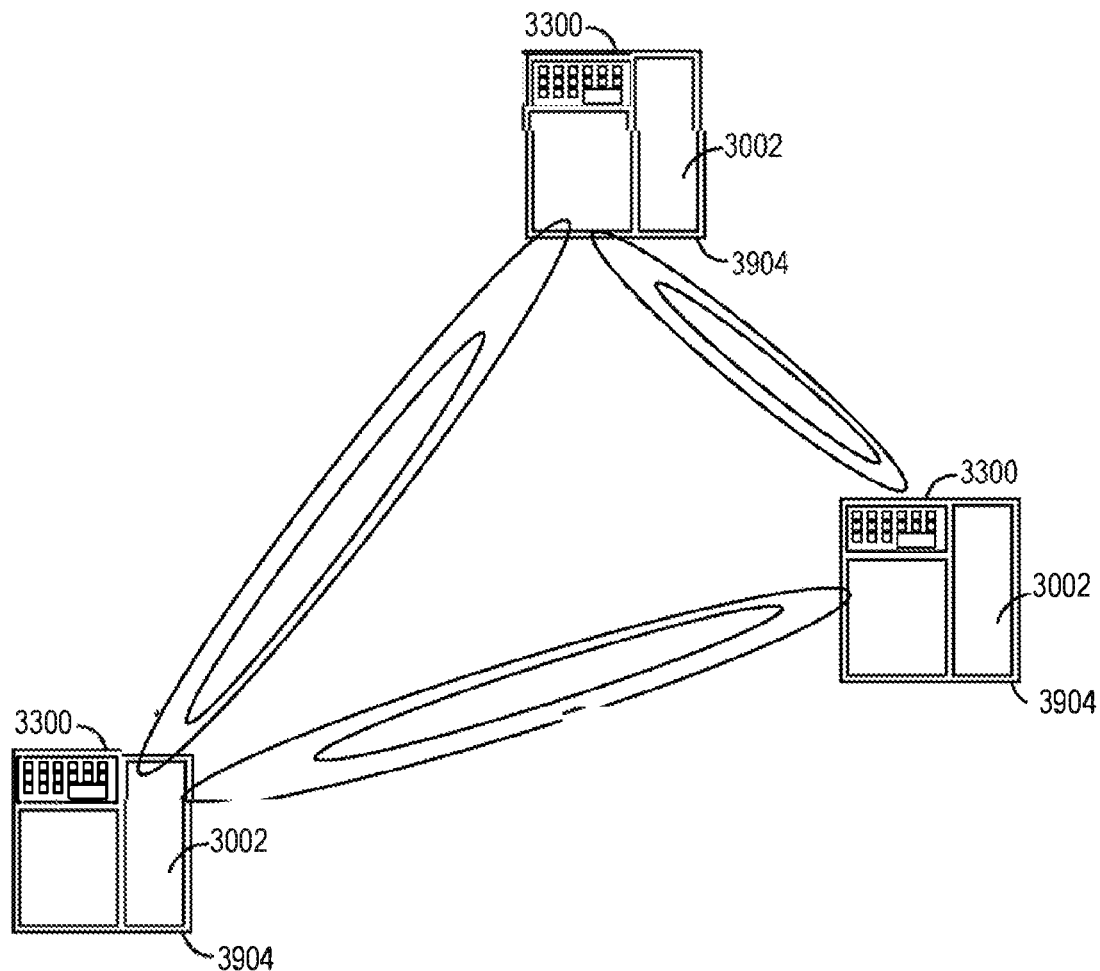
FIG. 41 illustrates a plurality of phone cases 3604 (or PCCCs 200) with antenna arrays 3300.

FIG. 41 illustrates a plurality of phone cases 3904 (or PCCCs 200) with antenna arrays 3300 which enable the devices 3904 to wirelessly communicated with each other to form a network in different wireless standards such as WiFi, Zigbee, Bluetooth, Long Term Evolution (LTE), LTE-Advanced (LTE-A), LTE-Unlicensed Spectrum (LTE-U), and/or LTE License Assisted Access (LTE-LAA), 4G, and/or 5G.

In this disclosure, devices that are described as in "communication" with each other or "coupled" to each other need not be in continuous communication with each other or in direct physical contact, unless expressly specified otherwise. On the contrary, such devices need only transmit to each other as necessary or desirable, and may actually refrain from exchanging data most of the time. For example, a machine in communication with or coupled with another machine via the Internet may not transmit data to the other machine for long period of time (e.g. weeks at a time). In addition, devices that are in communication with or coupled with each other may communicate directly or indirectly through one or more intermediaries.

Although process (or method) steps may be described or claimed in a particular sequential order, such processes may be configured to work in different orders. In other words, any sequence or order of steps that may be explicitly described or claimed does not necessarily indicate a requirement that the steps be performed in that order unless specifically indicated. Further, some steps may be performed simultaneously despite being described or implied as occurring non-simultaneously (e.g., because one step is described after the other step) unless specifically indicated. Moreover, the illustration of a process by its depiction in a drawing does not imply that the illustrated process is exclusive of other variations and modifications thereto, does not imply that the illustrated process or any of its steps are necessary to the embodiment(s), and does not imply that the illustrated process is preferred.

It should be noted that the recitation of ranges of values in this disclosure are merely intended to serve as a shorthand method of referring individually to each separate value falling within the range, unless otherwise indicated herein, and each separate value is incorporated into the specification as if it were individually recited herein. Therefore, any given numerical range shall include whole and fractions of numbers within the range. For example, the range "1 to 10" shall be interpreted to specifically include whole numbers between 1 and 10 (e.g., 1, 2, 3, . . . 9) and non-whole numbers (e.g., 1.1, 1.2, . . . 1.9). The word "about" when accompanying a numerical value is to be construed as indicating a deviation of up to and inclusive of plus or minus 50% from the stated numerical value (e.g., frequency of approximately 40 GHz shall mean in a frequency range of 20 GHz to 60 GHz and inclusive of fractions between 20 GHz to 60 GHz).

The foregoing description and embodiments have been presented for purposes of illustration and description and are not intended to be exhaustive or to limit the embodiments in any sense to the precise form disclosed. Also, many modifications and variations are possible in light of the above teaching. The embodiments were chosen and described to best explain the principles of the disclosure and its practical application to thereby enable others skilled in the art to best use the various embodiments disclosed herein and with various modifications suited to the particular use contemplated. The actual scope of the invention is to be defined by the following claims.

The invention claimed is:

1. A communication device comprising:
a first unit having a first antenna, a second antenna, and a first signal transmitting and receiving circuitry;
a second unit having a third antenna, a fourth antenna, and a second signal transmitting and receiving circuitry, wherein the second unit is located in proximity to the first unit;
wherein the first unit is capable of receiving signals at a first signal frequency at the first antenna in the frequency range of about 10 GigaHertz (GHz) to 300 GHz, passing the signal through an automatic gain controller to control the gain of the signals, down converting the signals to a second signal frequency in the frequency range of about 1 GHz to 9 GHz, and relaying the signals from the second antenna through a barrier to the second unit; and
wherein the second unit is capable of receiving the signals at the third antenna, passing the signals in the frequency range of 1 GHz to 30 GHz to the fourth antenna for transmission.

2. The device of claim 1, wherein the barrier is glass.

3. The device of claim 1, wherein the barrier is a glass window of a vehicle.

4. The device of claim 1, wherein the barrier is made of a dielectric material.

5. The device of claim 1, wherein the barrier is a panel of a vehicle.

6. The device of claim 1, further comprising:
a wireless power transmitter in the first unit and a wireless power receiver in the second unit; and
wherein the first unit is capable of wirelessly transmitting power from the wireless power transmitter to the wireless power receiver.

7. The device of claim 1, wherein the first unit and the second unit are magnetically coupled to each other on either side of the barrier.

8. The device of claim 1, wherein the barrier is a millimeter wave high transmission loss barrier.

9. The device of claim 1, wherein the barrier is glass.

10. The device of claim 1, wherein the first unit is attached to the outside building side of the barrier and the second unit is attached to the inside building side of the barrier.

11. The device of claim 1, wherein the second unit further comprises:
a power management unit to control transfer power from a second coil to a first coil in the unit.

12. The device of claim 11, wherein the first unit further comprises:
a power management unit connected to a battery and capable of controlling charging of the battery from the first coil.

13. The device of claim 1, wherein the first antenna and fourth antenna are antenna arrays arranged in a matrix.

14. A communication device comprising:
an outdoor unit having a first antenna and second antenna and first signal transmitting and receiving circuitry;
wherein the outdoor unit is capable of receiving signals in the frequency range of about 10 GigaHertz (GHz) to 100 GHz at the first antenna, passing the signal through an automatic gain controller to attenuate the signals, down converting the signals to the frequency range of about 1 GHz to 9 GHz, and transmitting from the second antenna through a barrier to an indoor unit;
wherein the indoor unit has a third antenna and a fourth antenna, and second signal transmitting and receiving circuitry, and a power transmitter, wherein the indoor unit is capable of receiving the frequency signals in the frequency range of about 1 GHz to 9 GHz at the third antenna and retransmitting in the range of about 1 GHz to 9 GHz from the fourth antenna; and wherein the indoor unit is capable of wirelessly transmitting power from the power transmitter to a power receiver located in the outdoor unit.

15. The device of claim 14, wherein the barrier is glass.

16. The device of claim 14, wherein the barrier is a glass window of a vehicle.

17. The device of claim 14, wherein the barrier is made of a dielectric material.

18. The device of claim 14, wherein the barrier is a panel of a vehicle.

19. The device of claim 14, wherein the first antenna and fourth antenna are antenna arrays arranged in a matrix.

20. A communication device comprising:
- an outdoor unit having a first antenna array and second antenna and first signal transmitting and receiving circuitry;
- wherein the outdoor unit is capable of receiving signals in the frequency range of about 10 GigaHertz (GHz) to 300 GHz at the first antenna array, passing the signals through an automatic gain controller to signals in the frequency range of about 1 GHz to 9 GHz for transmitting from the second antenna through a barrier to an indoor unit;
- wherein the indoor unit has a third antenna and a fourth antenna array, second signal transmitting and receiving circuitry and a power transmitter and wherein the indoor unit is capable of receiving the frequency signals in the frequency range of about 1 GHz to 9 GHz at the third antenna and retransmitting in the range of about 1 GHz to 9 GHz from the fourth antenna array; and
- wherein the indoor unit is capable of wirelessly transmitting power from the power transmitter to a power receiver located in the outdoor unit.

* * * * *